US012779142B2

(12) United States Patent
Ding et al.

(10) Patent No.: US 12,779,142 B2
(45) Date of Patent: Nov. 3, 2026

(54) UNIVERSAL ATOMIZER UTILIZING AN ELASTIC DRIVING FORCE

(71) Applicant: Innovate (Wuxi) Medical Technology Co., LTD, Wuxi City (CN)

(72) Inventors: Qi Ding, Wuxi City (CN); Chunxiao Hu, Wuxi City (CN); Bo Wu, Wuxi City (CN); Xiaoshan Li, Wuxi City (CN); Hong Gao, Wuxi City (CN)

(73) Assignee: Innovate (Wuxi) Medical Technology Co., LTD, Wuxi City (CN)

( * ) Notice: Subject to any disclaimer, the term of this patent is extended or adjusted under 35 U.S.C. 154(b) by 402 days.

(21) Appl. No.: 18/594,033

(22) Filed: Mar. 4, 2024

(65) Prior Publication Data

US 2024/0299675 A1 Sep. 12, 2024

(30) Foreign Application Priority Data

Mar. 6, 2023 (CN) ......................... 202310208453.2

(51) Int. Cl.
*A61M 11/00* (2006.01)

(52) U.S. Cl.
CPC ... *A61M 11/007* (2014.02); *A61M 2205/0216* (2013.01); *A61M 2205/0294* (2013.01)

(58) Field of Classification Search
CPC ........... A61M 11/005–008; A61M 2205/0216; A61M 2205/0294; A61M 16/208; B05B 9/04; B05B 9/047; B05B 9/0838; B05B 17/06; B05B 17/0607; B05B 17/0638; B05B 17/0646; B05B 17/0676
See application file for complete search history.

(56) References Cited

U.S. PATENT DOCUMENTS 2,009,575 A * 7/1935 Card, Jr. ................. F16K 21/04 251/339
2,764,324 A * 9/1956 Landreth .............. B67D 3/0009 277/606
3,209,785 A * 10/1965 Mercier .................... F15B 1/16 138/30
3,406,722 A * 10/1968 Ruth ..................... F16L 55/053 138/30

(Continued)

FOREIGN PATENT DOCUMENTS

CN 104028410 A * 9/2014 ......... B05B 17/0676
CN 207521218 U * 6/2018 ......... B05B 17/0646

(Continued)

*Primary Examiner* — Kathryn E Ditmer
(74) *Attorney, Agent, or Firm* — Che-Yang Chen

(57) ABSTRACT

An atomizer includes a medicament feeding unit, a medicament delivering vessel, and an atomizing unit, the medicament delivering vessel includes a medicament guiding tube communicated to the medicament feeding unit, and an elastic membrane bladder wound around the medicament guiding tube, wherein when medicament liquid is fed into the medicament delivering vessel through the medicament feeding unit, the elastic membrane bladder is inflated and is capable of generating an elastic driving force for driving the medicament liquid to be fed towards the atomizing unit for atomizing the medicament liquid. A depressurization receptacle has a curved medicament delivery passage is also provided for causing pressure loss of the medicament liquid.

19 Claims, 19 Drawing Sheets

(56) References Cited

U.S. PATENT DOCUMENTS 3,800,825 A * 4/1974 Zoll ........................ F16K 31/58 137/454.2
3,804,329 A * 4/1974 Martner .............. B05B 17/0607 366/127
3,884,242 A * 5/1975 Bazell ................. A61M 25/008 128/207.14
4,419,096 A * 12/1983 Leeper .................. A61M 5/152 222/215
4,915,693 A * 4/1990 Hessel .................. A61M 5/152 604/132
5,137,175 A * 8/1992 Kowalski ............. B67D 1/0462 222/105
5,303,853 A * 4/1994 Nye ..................... B65D 83/164 222/105
5,529,214 A * 6/1996 Lasonde ............ B65D 83/7711 222/105
10,086,166 B1 * 10/2018 Nashed ............. A61M 16/0891
2002/0185125 A1 * 12/2002 Klimowicz ....... A61M 15/0085 128/200.14
2003/0080214 A1 * 5/2003 Hess ................... B05B 17/0646 239/428.5
2004/0263567 A1 * 12/2004 Hess ................... B05B 17/0638 347/47
2005/0051162 A1 * 3/2005 Schuler ............... A61M 15/009 128/200.14
2005/0172956 A1 * 8/2005 Childers ........... A61M 15/0066 128/200.23
2012/0085449 A1 * 4/2012 Barth ......................... F15B 1/04 138/30
2013/0247902 A1 * 9/2013 Feriani .............. A61M 15/0091 128/200.16
2019/0366022 A1 * 12/2019 Leonard ............... A61M 11/005
2023/0276862 A1 * 9/2023 Greiner-Perth ......... A24F 42/20 131/273
2024/0246747 A1 * 7/2024 Scheuber ............... B65D 83/42

FOREIGN PATENT DOCUMENTS

KR 20220066467 A * 5/2022 ........ A61M 16/1075
WO WO-2015150721 A1 * 10/2015 ....... B29C 49/04114

* cited by examiner

UNIVERSAL ATOMIZER UTILIZING AN ELASTIC DRIVING FORCE

BACKGROUND OF THE PRESENT INVENTION

Field of Invention

The present invention relates to a medical atomizer, and more particularly to a universal atomizer which can operate effectively regardless of the placement orientation.

Description of Related Arts

A medical atomizer is a device that converts medicament liquid into aerosol for release. Conventional atomizers can be roughly divided into two types. One type is a relatively large atomizer device which has a large volume and is not used in conjunction with a mechanical ventilation equipment. Instead, it has an internal pressurization device to work with an atomizing unit, so that atomized medicament is ultimately discharged through the help of the pressurization device.

The other type is a small atomizer which is generally connected to a breathing circuit arrangement. The medicament liquid comes into contact with the atomizer (mostly using a vibrating mesh) because of the gravity of the liquid itself, so that the vibrating mesh converts the medicament liquid into aerosol medicament, which is then supplied to the patient through the breathing circuit arrangement.

However, the conventional atomizers have an unavoidable problem, which is the lack of an internal liquid pressurization device. All the medicament liquid can only come into contact with the mesh nebulizer through gravity. This also means that the medicament liquid in conventional atomizers must be in a vertical direction (along the gravity line) with the vibrating mesh. Once tilted, the stability of its operation will be greatly affected. At the same time, the structural characteristics of small atomizers also require the center of gravity of the atomizer itself to be located above the position of the breathing circuit arrangement. If the small atomizer is not properly fixed, the operation of atomization will be extremely unstable.

As an example, a Chinese invention patent application, which has an application number CN201810447186.3, titled “medical nebulizer”, application date May 1, 2018, has disclosed a conventional medical atomizer. During its operation, an atomizing cup body, an atomizing unit, and a mouthpiece must all be aligned along the gravity line in order to function. Once inverted, it will be unable to operate, and tilting will also result in incomplete contact between the liquid in the atomizing cup body and the atomizing unit, greatly reducing the atomization efficiency.

As another example, a Chinese invention patent application, which has an application number CN201310330959.7, titled “portable medical nebulizer”, application date Aug. 1, 2013, has disclosed another conventional medical atomizer. During its use, it must be ensured that the empty cavity container and the mesh nebulizer are in a predominantly vertical position. Once excessively tilted or inverted, the electric circuit will be disconnected and the mesh nebulizer will stop working. This avoids the continual working problem of the mesh nebulizer, but fundamentally fails to solve the issue of incorrect placement of the nebulizer affecting normal atomization operation.

SUMMARY OF THE PRESENT INVENTION

In view of the above-mentioned deficiencies in the prior art, the present invention provides an universal atomizer comprising an outer shell, a medicament feeding unit, an atomizing unit, a medicament delivering vessel in communication with the medicament feeding unit and a depressurization receptacle in communication with the medicament delivering vessel which is capable of generating an elastic force.

The atomizing unit is set at the atomizing port of the depressurization receptacle, and the atomizing unit is provided with a mist outlet for connecting with a breathing circuit arrangement.

The medicament delivering vessel comprises an elastic membrane bladder that provides a driving power for the discharge of the liquid.

The depressurization receptacle is provided with a pressure relief structure, and the pressure relief structure comprises a plurality of medicament delivery channels. The medicament liquid in the medicament delivering vessel is discharged through a plurality of the medicament delivery channels and converges in the same plane. The plurality of medicament delivery channels is symmetrically distributed or uniformly distributed around a center.

Preferably, the number of medicament delivery channels is even and there are arranged with a symmetrical distribution. The dispensing directions of two symmetrical medicament delivery channels are aligned with each other.

Preferably, the number of medicament delivery channels is odd and the are uniformly distributed around a center, and the medicament delivery channels of the uniformly distributed medicament delivery channels converge at the center.

The preferred elastic medicament liquid container further comprises a medicament guiding tube, and the elastic membrane bladder is a tubular elastic membrane bladder, which is fixedly wrapped around the medicament guiding tube. The two ends of the medicament guiding tube are respectively connected to the medicament feeding unit and the depressurization receptacle. The medicament guiding tube is provided with a liquid passage hole Preferably, the proximal end of the medicament guiding tube adjacent to the atomizing unit comprises a multi-channel structure, the multi-channel structure comprises a side channel n communication with the outside and one or more branch channels leading to the atomizing unit. The side channel is embedded with a film that is water stopping while is gas permeable, and each branch channel is provided with a medicament outlet near one end of the atomizing unit, and a diversion projection is set at the top of the branch channels. The diversion projection abuts against the atomizing unit and couples with the branch channels to form a plurality of the medicament delivery channels.

Preferably, the outer wall of the medicament guiding tube is provided with a plurality of protruding rings for fixing and sealing the elastic membrane bladder.

Correspondingly, the end walls of the elastic membrane bladder are thick, and the inner diameter of the elastic membrane bladder is smaller than the outer diameter of the wrapped portion of the medicament guiding tube, and the elastic membrane bladder is tightly wound around the protruding rings at the outer side of the outer wall of the medicament guiding tube; the middle wall of the elastic membrane bladder is thinner and is covering and wrapping the outer side of the liquid passage hole in the middle section of the medicament guiding tube.

The elastic membrane bladder can be made of PET or silicone material.

Preferably, the atomizing unit comprises a vibrating mesh, and the positive and negative electrodes of the vibrating mesh are connected to a socket interface on a side wall of the outer shell.

Preferably, the contact surface between the atomizing unit and the outer shell, and the contact surface between the atomizing unit and the medicament guiding tube, are respectively provided with elastic sealing rings.

The connecting surface between the medicament feeding unit and the medicament delivering vessel is provided with a sealing ring.

Preferably, the outer shell is provided with an inlet connection port, and an outlet connection port which are connected to the breathing circuit arrangement.

The universal atomizer of the present invention has the following beneficial effects.

By the contraction of the elastic membrane bladder to supply pressure to the medicament liquid, the requirement for gravity is eliminated. Regardless of the angle at which the atomizer of the present invention is placed, the medicament liquid can be atomized, fundamentally solving the problem of the placing position of the conventional atomizer will determine whether the conventional atomizer can function properly.

By increasing the hydraulic pressure of the medicament liquid through the elastic membrane bladder, and then reducing the pressure by multiple medicament delivery channels to regulate the medicament liquid pressure at the depressurization receptacle, the continuous and stable operation of the atomizing unit is ensured.

The design of the multi-path structure can assist in the discharge of gas generated during the operation of the atomizing unit.

According to another aspect, the present invention provides an atomizer comprising a medicament feeding unit, a medicament delivering vessel, and an atomizing unit, wherein when the medicament liquid is fed into the medicament delivering vessel through the medicament feeding unit, the medicament delivering vessel is capable of generating an elastic driving force for driving the medicament liquid to be fed towards the atomizing unit for atomizing the medicament liquid.

Preferably, the medicament delivering vessel comprises a medicament guiding tube communicated to the medicament feeding unit, and an elastic membrane bladder wrapped around the medicament guiding tube, wherein an inflating chamber is defined between the elastic membrane bladder and the medicament guiding tube, wherein the medicament guiding tube has a guiding channel and one or more liquid passage holes communicating the guiding channel to the inflating chamber.

Preferably, the elastic membrane bladder comprises a middle section and two end sections connected to two ends of the middle section, wherein a thickness of the middle section is smaller than a thickness of each of the two end sections.

Preferably, the medicament guiding tube comprises one or more retaining rings at each of two ends thereof for frictional engagement with the corresponding end section of the elastic membrane bladder.

Preferably, each of the retaining rings has gradually reducing diameters along a direction towards the one or more liquid passage holes.

Preferably, an inner diameter of the elastic membrane bladder is smaller than or equal to an outer diameter of the medicament guiding tube.

Preferably, a material of the elastic membrane bladder is one of silicon material and polyethylene terephthalate.

Preferably, the atomizer further comprises a depressurization receptacle connected to the medicament guiding tube, wherein the depressurization receptacle has a curved medicament delivery passage for causing pressure loss of the medicament liquid, wherein the curved medicament delivery passage is communicated to the medicament delivering vessel for feeding the medicament liquid toward the atomizing unit.

Preferably, the curved medicament delivery passage comprises a receiving chamber communicated to the medicament delivering vessel and a plurality of branch channels communicated to the receiving chamber, and an atomizing area communicated to the plurality of branch channels, wherein the atomizing unit is facing towards the atomizing area.

Preferably, the depressurization receptacle comprises a receptacle body comprising an end surface, and a plurality of diversion protrusions protruded from the end surface to define the atomizing area.

Preferably, the curved medicament delivery passage comprises a plurality of diversion channels each is formed between two adjacent diversion protrusions.

Preferably, the plurality of diversion channels is configured in a manner that liquid flows of the medicament liquid collide with each other to form a balance zone in the atomizing area at a center of the plurality of diversion channels arranged in a circumferential direction.

Preferably, the plurality of diversion channels is evenly distributed along the circumferential direction and allow the liquid flows to converge in a same plane of the atomizing area.

Preferably, the plurality of diversion channels is grouped in pairs, where the two diversion channels of each pair are symmetrically arranged with each other.

Preferably, the depressurization receptacle further comprises a first sealing ring provided between the end surface of the receptacle body and the atomizing unit, wherein the atomizing area is formed within the first sealing ring.

Preferably, an extending direction of each of the branch channels is vertical to a plane of the atomizing area.

Preferably, the curved medicament delivery passage further comprises one or more side channels communicated to the receiving chamber, wherein each of the one or more side channels is provided with a gas permeable film that is water stopping for dispersing air bubbles generated in the depressurization receptacle to the outside.

Preferably, the depressurization receptacle further comprises one or more mounting members for mounting the one or more gas permeable films at the one or more side channels respectively, wherein each of the one or more mounting members has a through hole for communicating the corresponding gas permeable film to the outside.

Preferably, the medicament feeding unit comprises a sealing housing, a sealing plunger arranged in the sealing housing, a resilient valve ring, and a spring which is connected to the sealing plunger and the sealing housing, wherein the wherein the medicament feeding unit has an injection port and a feeding passage, wherein the sealing plunger comprises a plunger rod and an abutting ring connected to the plunger rod, the sealing housing has an inner step, the resilient valve ring is provided between the inner step of the sealing housing and the abutting ring of the sealing plunger, so that the injection port communicated to the feeding passage between the sealing plunger and the sealing housing is capable of being sealed by the resilient valve ring.

Preferably, the atomizing unit comprises an atomizing layer and a ring-shaped piezoelectric ceramic layer stacked on the atomizing layer.

DETAILED DESCRIPTION OF THE PREFERRED EMBODIMENT

Figure 1:
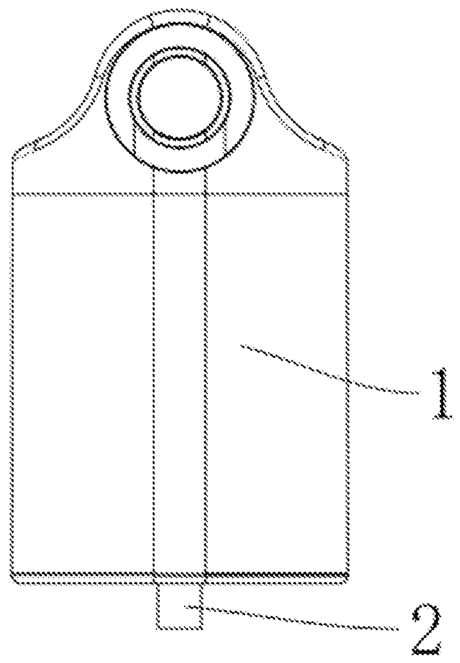
FIG. 1 is a front perspective view of a universal atomizer according to a first preferred embodiment of the present invention.
Figure 2:
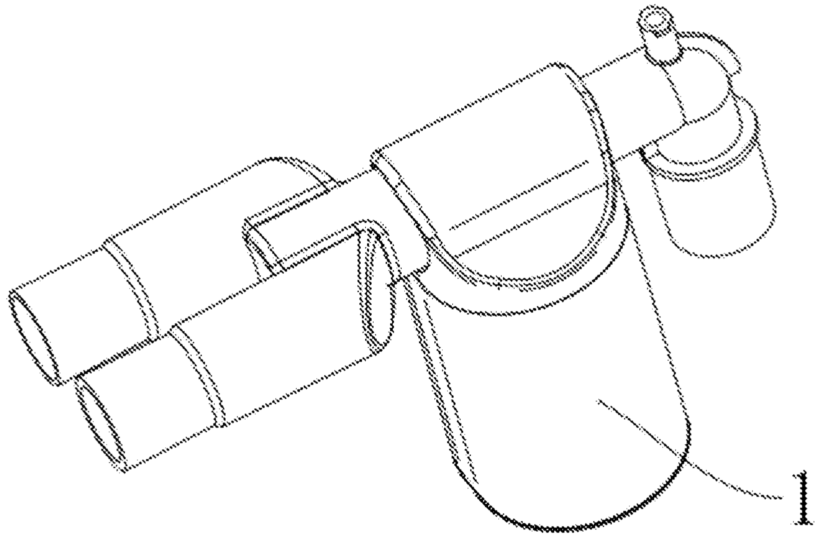
FIG. 2 is a perspective view illustrating the universal atomizer being connected to a breathing circuit arrangement according to the first preferred embodiment of the present invention.

As shown in FIGS. 1-14, a universal atomizer according to a first preferred embodiment of the present invention comprises an outer shell 1 at the outside, a medicament feeding unit 2, an atomizing unit 4, a medicament delivering vessel 3 in communication with the medicament feeding unit 2 and a depressurization receptacle 5 in communication with the medicament delivering vessel 3 which is capable of generating an elastic driving force.

The medicament is injected into the medicament delivering vessel 3 from the medicament feeding unit 2 through an injector, and finally converges at the depressurization receptacle 5, the atomizing unit 4 is provided at an atomizing port of the depressurization receptacle 5, and a mist outlet 40 is provided at the atomizing unit 4 for communication with a breathing circuit arrangement, the converged medicament contacts with the atomizing unit 4 and is atomized into fine mist by the atomizing unit 4, and finally enters the breathing circuit arrangement through the mist outlet 40 and is inhaled by a patient.

The breathing circuit arrangement is a generic term for describing the pipeline equipment used by the patient for breathing during mechanical ventilation. The medicament mist atomized by the atomizing unit 4 will be discharged into the breathing circuit arrangement and directly inhaled by the patient.

The essential structure of the medicament feeding unit 2 is a medical valve structure comprising but not limited to a pressure injection valve, a three-way valve, a check valve, and an infusion switch.

Figure 3:
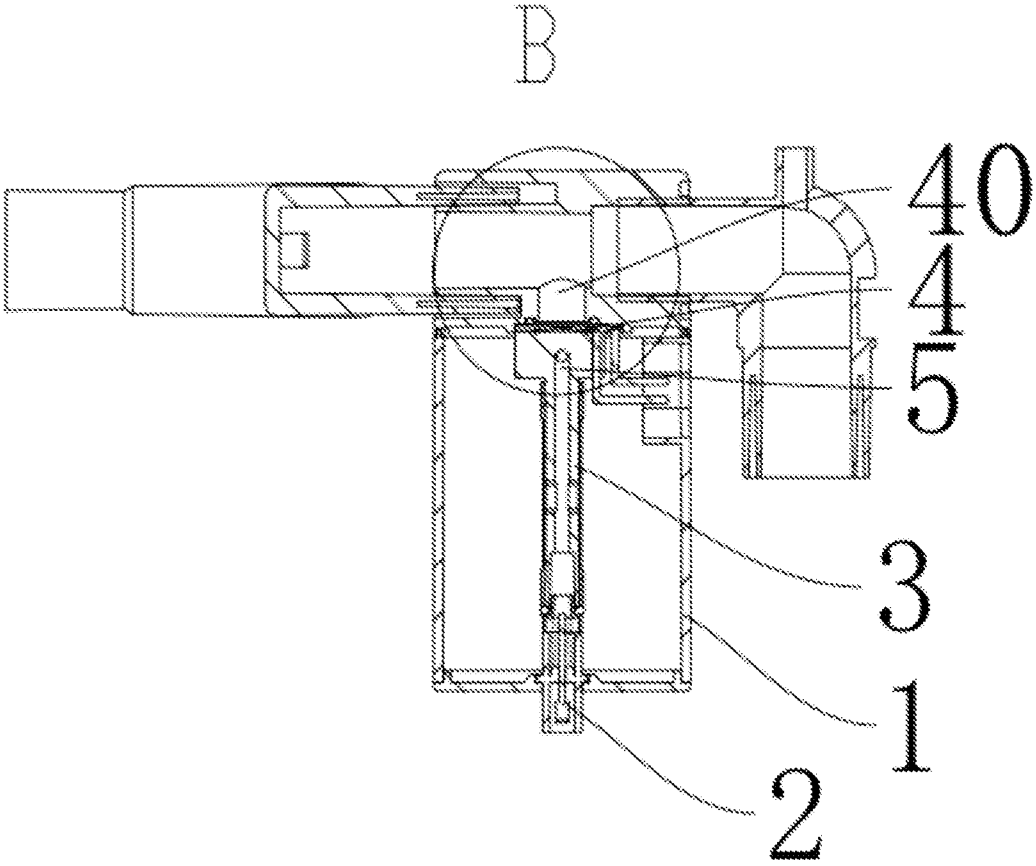
FIG. 3 is a cross-sectional view of the universal atomizer of FIG. 2.
Figure 7:
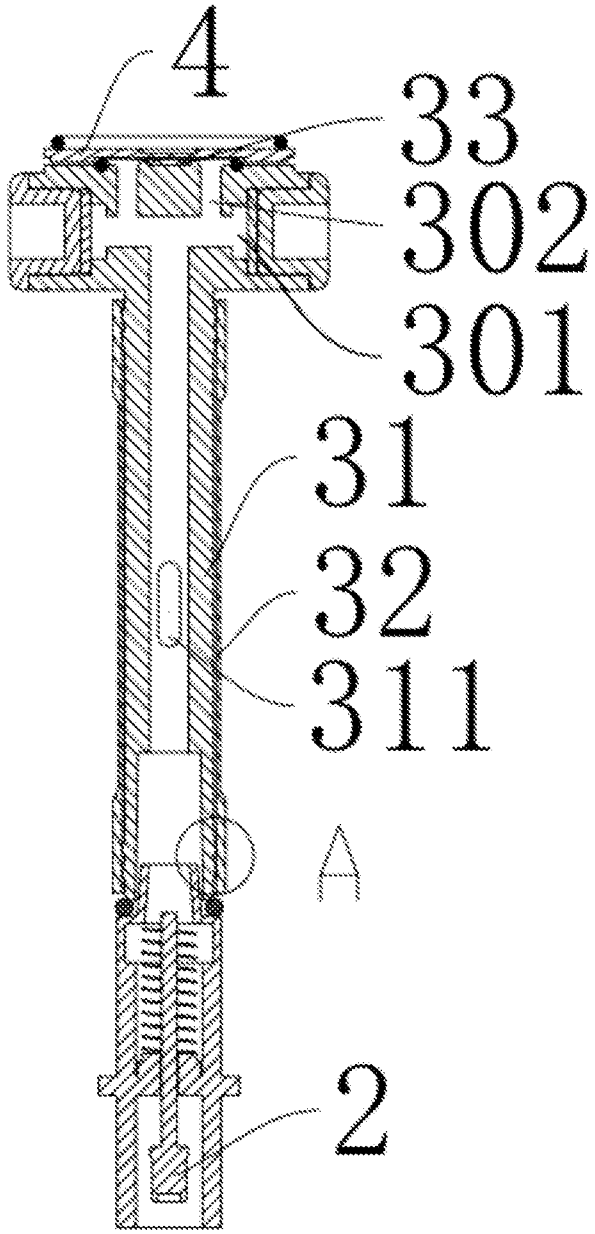
FIG. 7 is a cross-sectional view illustrating the internal structure of parts of the universal atomizer according to the first preferred embodiment of the present invention.
Figure 8:
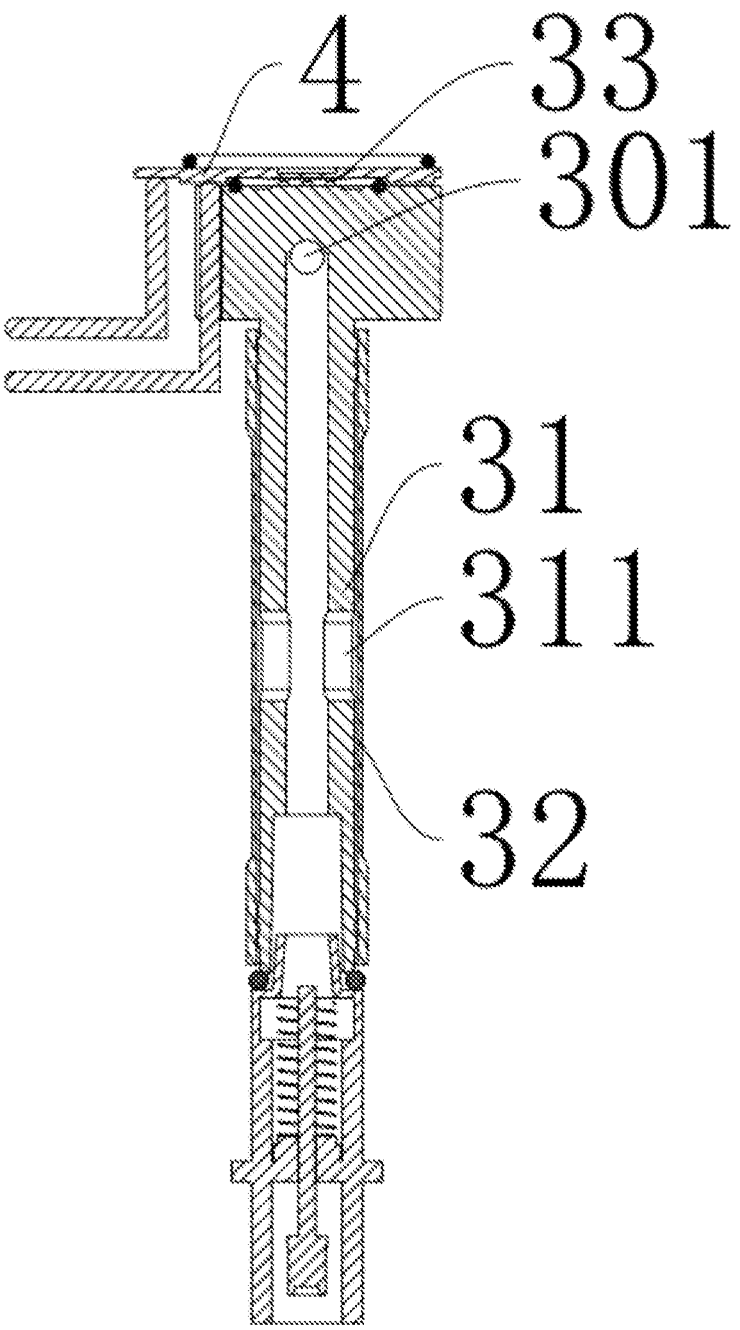
FIG. 8 is a longitudinal sectional view illustrating the internal structure of parts of the universal atomizer according to the first preferred embodiment of the present invention.

Referring to FIG. 3, FIG. 7, and FIG. 8, in the present invention, the medicament feeding unit 2 adopts a pressure injection valve which is essentially a check valve structure.

The structure of the pressure injection valve comprises a sealing housing embedded at an injection port of the outer shell for fixed connection with the outer shell 1, a sealing plunger arranged inside the sealing housing, and the sealing plunger is limited by a spring on one side inside the sealing housing.

Under normal conditions, the spring is fitted on the outside of the sealing plunger, with one end abutting against an inner cavity wall of the sealing housing and the other end abutting against a sealing ring of the sealing plunger, so that the sealing ring abuts the injection port of the inner cavity of the sealing housing, thereby blocking the communication between the inner cavity of the sealing housing and the outside.

When the syringe is inserted through the injection port, the spring is compressed, and the sealing ring is separated from the injection port, allowing the liquid to flow through the gap between the injection port and the sealing plunger into the medicament delivering vessel 3. When the syringe is removed from the injection port, the spring returns to its original position, and the pressure injection valve returns to its normal state.

The medicament delivering vessel 3 comprises an elastic membrane bladder 32 that provides driving power for the discharge of the medicament liquid which is stored in the elastic membrane bladder 32 through the medicament feeding unit 2. The thickness range of the elastic membrane bladder 32 for medicament storage is 0.08-0.8 mm, and the actual amount of medicament that can be accommodated is 5 ml-20 ml. The internal hydraulic pressure is 0-170 mmHg. The commonly used amount of nebulized medicament liquid for patients is 10 ml, and the hydraulic pressure inside the elastic membrane bladder 32 is 115-140 mmHg.

Figure 4:
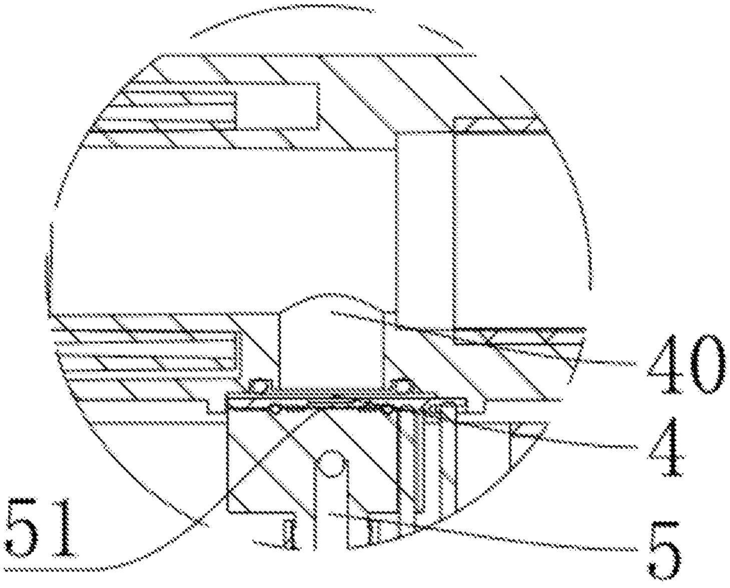
FIG. 4 is an partial enlarged view of part B in FIG. 3.
Figure 5:
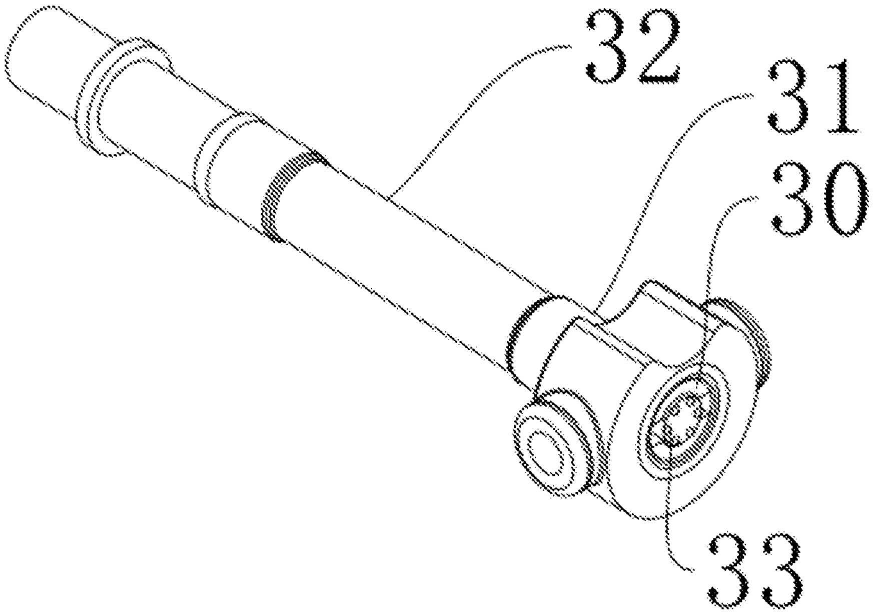
FIG. 5 is a perspective view illustrating parts of a elastic medicament chamber element of the universal atomizer according to the first preferred embodiment of the present invention.
Figure 6:
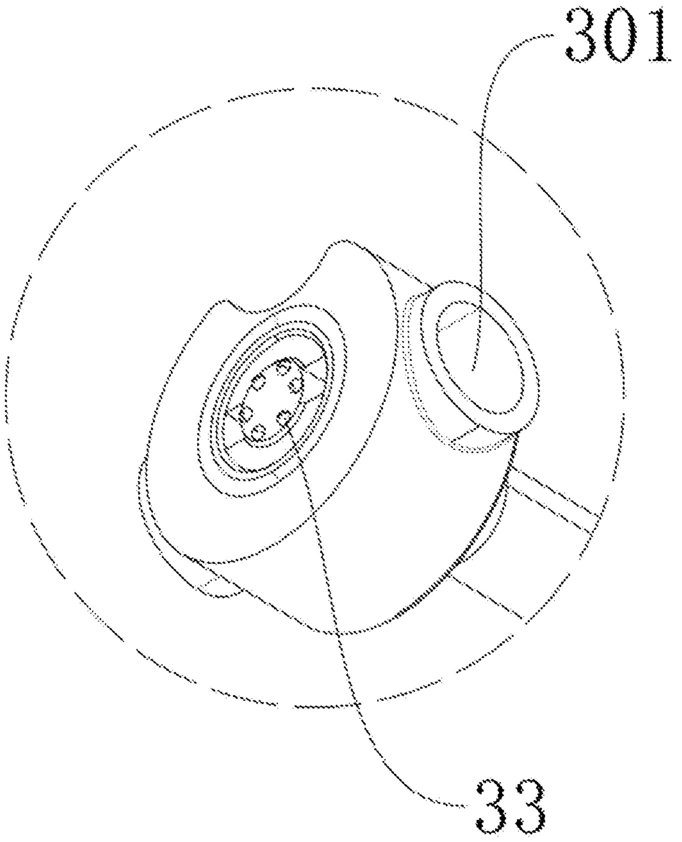
FIG. 6 is a schematic view illustrating a diversion protrusion of the universal atomizer according to the first preferred embodiment of the present invention.

Since the atomizing unit 4 needs to work in a certain environment, referring to FIG. 4, a through-type nebulizer which is vibrating mesh is used herein, which uses electronic ultrasonic oscillation (oscillation frequency is 1.7 MHz, beyond the range of human hearing, harmless to humans and animals). Through the high-frequency resonance of the nebulizer, water is thrown off the water surface to produce naturally floating water mist.

In case of excessive pressure, the high-frequency resonance will be affected, and when the strong pressure state is maintained for about 30 s, it will cause the inability for maintaining effective vibration, so it needs to be combined with the depressurization receptacle 5 for pressure relief treatment.

Referring to FIGS. 3 and 4, a decompression structure is provided in the depressurization receptacle 5. The decompression structure has one or more medicament delivery channels 51. The medicament in the medicament delivering vessel 3 is discharged through the medicament delivery channels 51 and converges in the same plane. In order to prevent direct impact of the medicament on the atomizing unit 4, the medicament delivery channels 51 are symmetrically distributed or uniformly distributed around the center. In this case, when the medicament is divided into flows in multiple pipelines, dead water zones or vortex zones are formed due to changes in cross-section and the presence of corners, ultimately achieving the purpose of pressure loss.

When multiple medicament delivery channels 51 are symmetrically or uniformly distributed around the center, the outflow of liquid will form a vortex after entering the same plane. At the same time as the pressure is reduced again, it also cooperates with the atomization process of atomizing unit 4, ultimately achieving the pressure dynamic balance.

When the atomizing unit 4 is embodied as a vibrating mesh. The maximum pressure during normal operation must be less than 155 mmHg. Once exceeded, it will cause difficulty in vibrating the vibrating mesh and make atomization difficult. After the pressure loss through the medicament delivery channels 51, the pressure is generally maintained between 135-145 mmHg (with fluctuations of 0-2 mmHg depending on the placement position).

It should be stated here that after the medicament liquid is injected into the medicament delivering vessel 3, it will directly be fed into the depressurization receptacle 5. At this time, the pressure is in an overloaded state, but it will not damage the atomizing unit 4 itself and its initial working state. Once the atomizing unit 4 starts working, the liquid starts to flow, and the hydraulic pressure near the atomizing unit 4 will decrease significantly, and the atomizing unit 4 will also enter a normal working mode.

The two ways of configuring and distributing the medicament delivery channels 51 are described in the following description.

When the number of the medicament delivery channels 51 is even, they are symmetrically distributed, and the medicament dispensing ports of two symmetrically distributed medicament delivery channels 51 are respectively aligned withe each other.

The medicament delivery channels 51 are grouped in pairs, and the liquid flows collide and cancel each other out, forming a balance zone in the center. In this balance zone, from the outside to the center, the pressure gradually decreases, and the liquid flow also slows down gradually. This corresponds to the working area of the vibrating mesh from low to high efficiency under normal conditions. Under the continuous operation of the vibrating mesh, the medicament liquid at the center is efficiently atomized, forcing the continuous flow of the medicament liquid to form a dynamic balance. When multiple sets of medicament delivery channels 51 are evenly distributed around the center of the vibrating mesh, it will form a dynamic balance that is beneficial to the overall situation, so as to facilitate the normal operation of the atomizing unit 4.

Alternatively, if the number of the medicament delivery channels 51 is odd, they are evenly distributed around a center, and the medicament dispensing ports of the evenly distributed medicament delivery channels 51 converge at the center.

The medicament dispensing channels 51 are uniformly distributed around the center or symmetrically distributed, so that the medicament liquid flowing out of the medicament dispensing ports will form a vortex or collide with each other, eventually forming a balanced region in the center. This balanced region has similar functions and results as mentioned above.

It should be noted that the structure of the vibrating mesh is disc-shaped, and the most efficient working area is located in the center, which corresponds exactly to the above-mentioned balanced region.

Figure 10:
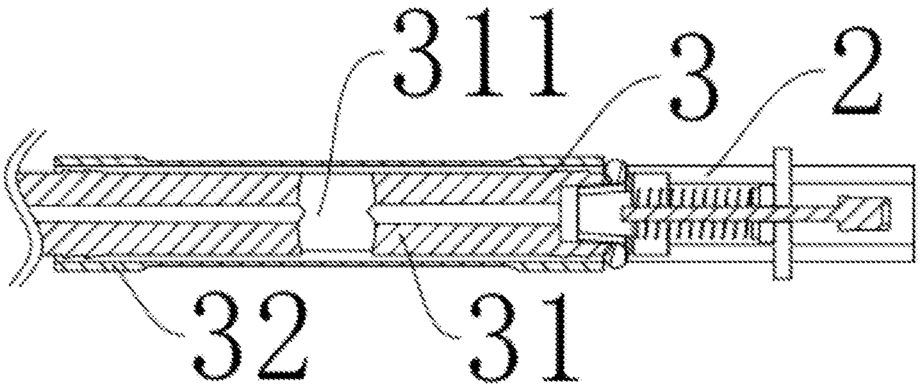
FIG. 10 is a schematic view illustrating the elastic membrane bladder structure under normal conditions according to the first preferred embodiment of the present invention.

Referring to FIGS. 7, 8, and 10, in the first preferred embodiment of the present invention, the medicament delivering vessel 3 also comprises a medicament guiding tube 31, and the elastic membrane bladder 32 is a tubular elastic membrane bladder which is fixed around the medicament guiding tube 31 and communicated with the medicament feeding unit 2 and the depressurization receptacle 5 at both ends of the medicament guiding tube 31, and the medicament guiding tube 31 is provided with a liquid passage hole 311 which penetrates the side wall of the medicament guiding tube 31.

Figure 11:
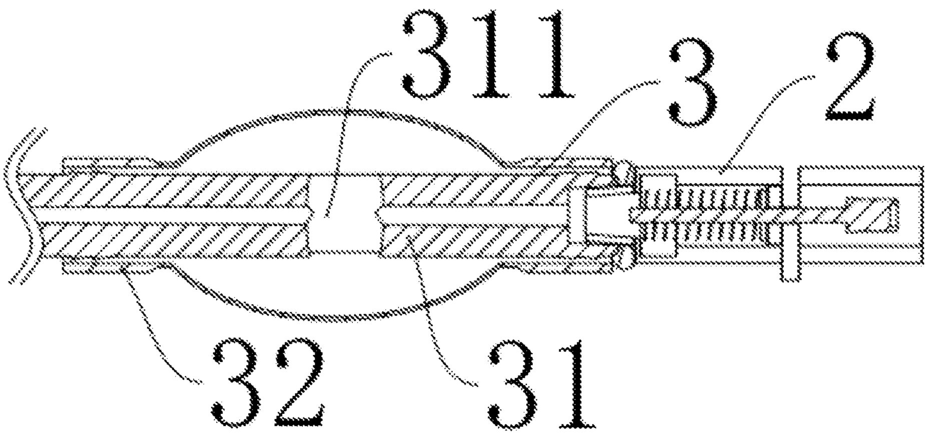
FIG. 11 is a schematic view illustrating the elastic membrane bladder structure after medicament injection according to the first preferred embodiment of the present invention
Figure 12:
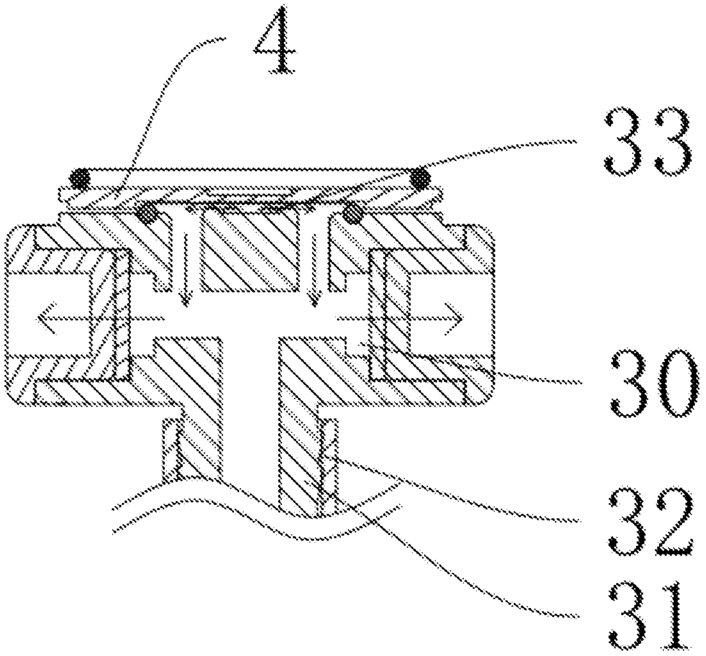
FIG. 12 is a schematic view illustrating the liquid flow direction in the decompression and exhaust passage of the universal atomizer according to the first preferred embodiment of the present invention.
Figure 13:
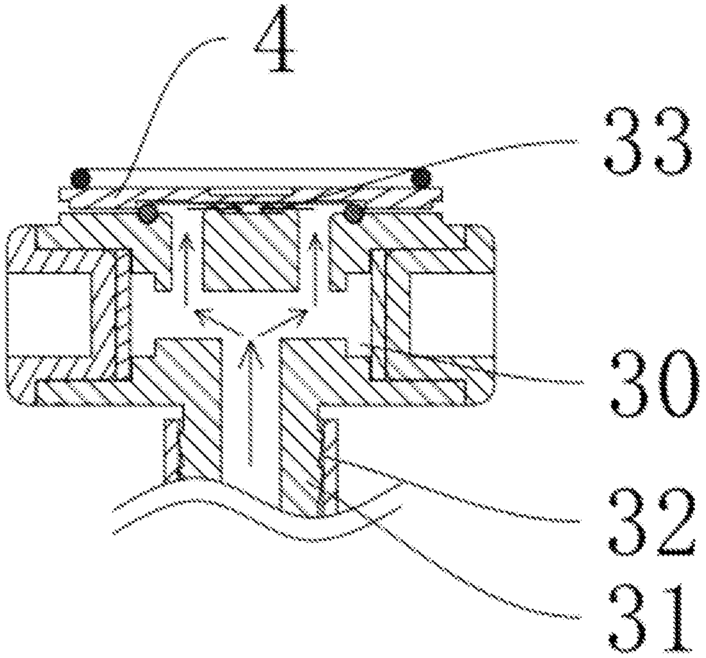
FIG. 13 is a schematic view illustrating the liquid flow direction of the medicament delivery channels of the universal atomizer according to the first preferred embodiment of the present invention.

Referring to FIGS. 10 and 11, the medicament liquid flows into the medicament guiding tube 31 from the medicament feeding unit 2 and is stored in the elastic membrane bladder 32 through the liquid passage hole 311 penetrating through the side wall of the medicament guiding tube 31. When the medicament liquid is injected into the elastic membrane bladder 32, it will expand and bulge, so as to present a water ball shape and form a liquid storage chamber.

The medicament guiding tube 31 has a tubular shape, with one end in contact with the atomizing unit 4 for cooperation, and the other end connected to the medicament feeding unit 2 for medicament liquid delivering. During the nebulization process, the elastic membrane bladder 32 supplies hydraulic pressure through its own elasticity and continuously shrinks, but always confines the medicament liquid. During the shrinking process, the supply pressure of the elastic membrane bladder 32 is unstable, which is due to the instability of the liquid flow direction and the instability of the supply pressure.

In order to maintain the stability of the supply pressure, that is, to prevent excessive pressure in the initial supply pressure state, a flow direction change is formed by the liquid passage hole 311 at the side wall of the medicament guiding tube 31, forcing the occurrence of a dead water area or a vortex area, and causing pressure loss. The greater the initial pressure, the greater the pressure loss, and the final supply pressure will be within a certain range.

The tubular structure of the medicament guiding tube 31 itself will guide the liquid flow during the convergence process of the elastic membrane bladder 32, ultimately align the direction of the pressure. Finally, the medicament liquid and the atomizing unit 4 are always in an effective contacting state.

Referring to FIGS. 3, 4, 5, 6, 7, 8, and 14, based on the above-mentioned medicament delivering vessel 3, the preferred solution for the medicament delivery channels 51 in the depressurization receptacle 5 is embodied to have a following configuration.

An end of the medicament guiding tube 31 adjacent to the atomizing unit 4 comprises a multi-channel structure 30 which has a side channel 301 communicated to the outside and one or more branch channels 302 leading to the atomizing unit 4. The side channel 301 is embedded with a water stopping film that allows gas to pass through, and the branch channels 302 adjacent to one end of the atomizing unit 4 is provided with a medicament liquid outlet and a diversion protrusion 33 is set on the top. The diversion protrusion 33 is in contact with the atomizing unit 4 and is adjacent to the branch channels 302 to form the medicament delivery channels 51.

According to this embodiment, the structure of the depressurization receptacle 5 comprises two parts. One part is located inside the medicament guiding tube 31, that is, the multi-channel structure 30. The other part is the gap between the medicament guiding tube 31 and the atomizing unit 4. The composition of the wall for forming the gap comprises a bottom surface of the atomizing unit 4, a top surface of the branch channels 302, a sealing ring, and the diversion protrusion 33 located at the top of the medicament delivering vessel 3.

The depressurization receptacle 5 also comprises two functional parts, one functional part is the medicament delivery channels 51 for delivering the medicament liquid, and the other functional part is the pressure reduction and exhaust channel for discharging gas and forming a dead water zone.

Referring to FIGS. 5, 6, 7, 8, and 13, the structure of the medicament delivery channels 51 is divided into two parts. One part is the branch channels 302 in the multi-channel structure 30, and the other part is the gap and the medicament outlet after the diversion protrusion 33 is aligned with the atomizing unit 4.

Figure 14:
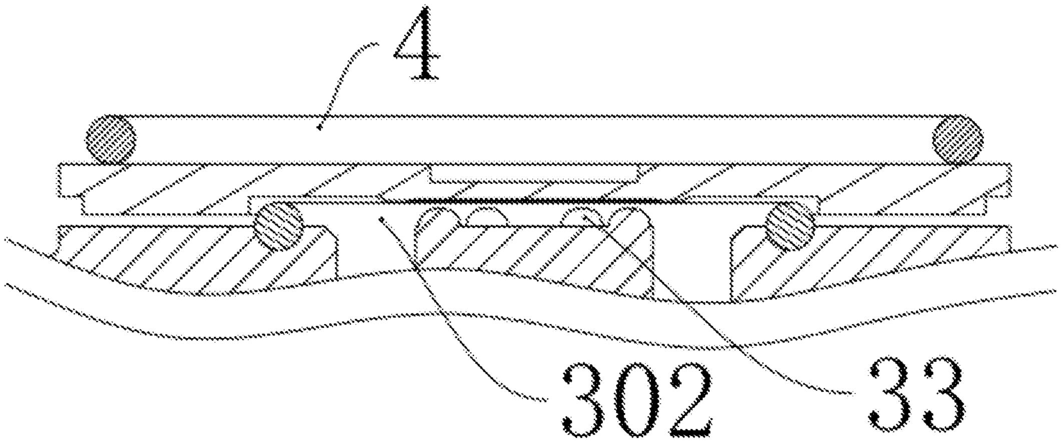
FIG. 14 is a schematic view illustrating the path towards the atomizing unit of the universal atomizer according to the first preferred embodiment of the present invention.
Figure 15:
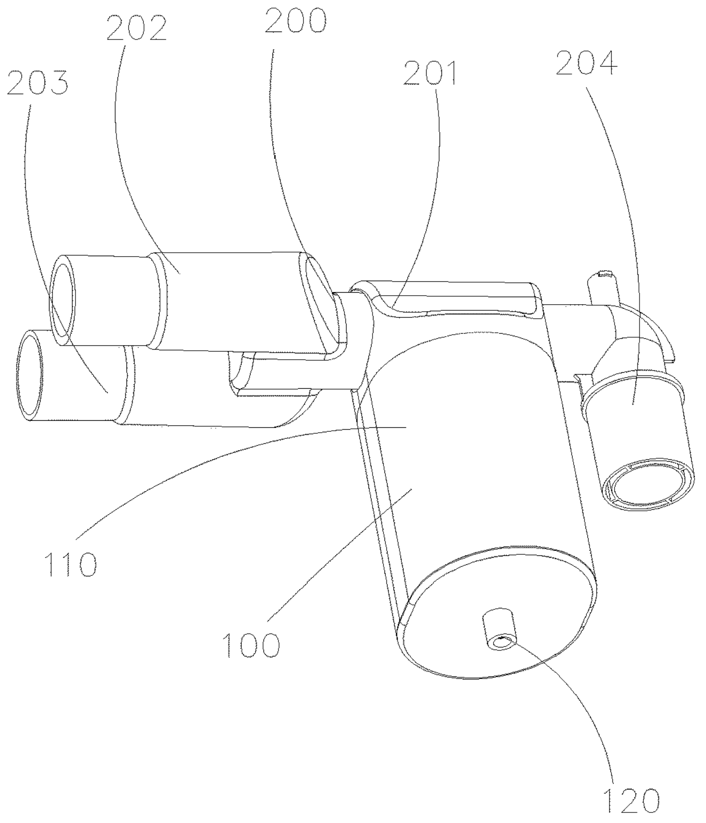
FIG. 15 is a perspective view of an universal atomizer being connected to a breathing circuit arrangement according to a second preferred embodiment of the present invention.
Figure 16:
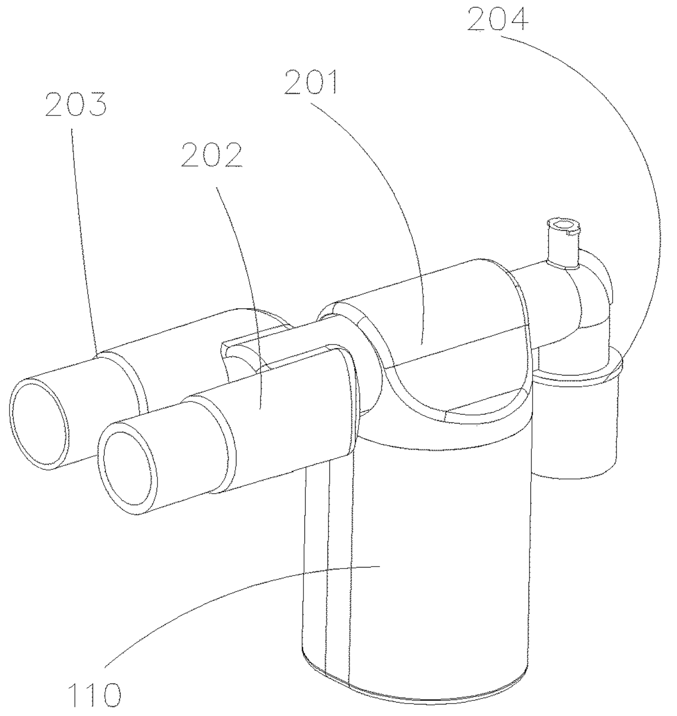
FIG. 16 is another perspective view of the universal atomizer being connected to the breathing circuit arrangement according to the second preferred embodiment of the present invention.

Referring to FIG. 14, the medicament liquid flows out of the elastic membrane bladder 32 and enters the medicament guiding tube 31. When it flows through the branch channels 302, it causes pressure loss and eventually gathers in the cavity. At this time, the diversion protrusion 33 and the atomizing unit 4 come into contact, forming individual medicament outlets. The medicament liquid flowing out from the medicament outlets converges at the center and eventually forms a vortex and work together with the atomizing unit 4 for atomization.

When the atomizing unit 4 starts working, the medicament liquid is atomized and then the mist enters the breathing circuit arrangement through the atomizing unit 4, and the liquid in the elastic membrane bladder 32 is supplemented into the atomizing unit 4. During this process, there is continuous hydraulic loss, forming a dynamic balance.

Referring to FIGS. 5, 6, 7, 8, and 12, in this embodiment, the medicament delivery channels 51 comprises two vertical bends, eight diversion protrusions 33 for pressure distribution, and dead zones on both sides. The final pressure loss is approximately 13%-15%. When the maximum medicament volume is 20 ml, the pressure inside the elastic membrane bladder 32 is 180 mlHg, and the pressure at the medicament outlet is approximately 150 mlHg, which meets the normal working requirements of the vibrating mesh.

Referring to FIGS. 5, 6, 7, 8, and 12, the structure of the decompression exhaust passage is divided into two parts. One part is the gap and the diversion outlets (also the medicament outlet of the aforementioned medicament delivery channels 51) formed by the diversion protrusion abutting against the atomizing unit 4. The other part is the side channel 301.

Under normal circumstances, when atomization is occurring, the air entering the gap from the outside will accumulate and affect the operation of atomizing unit 4. However, by setting diversion ports here, it will work in conjunction with the vibration of the mesh of the atomizing unit 4 itself to disperse the tiny bubbles and force the bubbles to flow out from the diversion port. Due to the flow of the liquid, it will eventually converge in the multi-channel structure 30, and most of it will be discharged through the water stopping gas permeable film inside the side channel 301, while a small amount will accumulate and continue to be gradually discharged after reaching a certain level of accumulation. The amount of air remaining in the multi-channel structure 30 is very small and will not affect the normal operation of the atomizer itself.

Some of the medicament located in the side channel 301 will form a dead water area, assisting in reducing the hydraulic pressure of the medicament.

Figure 9:
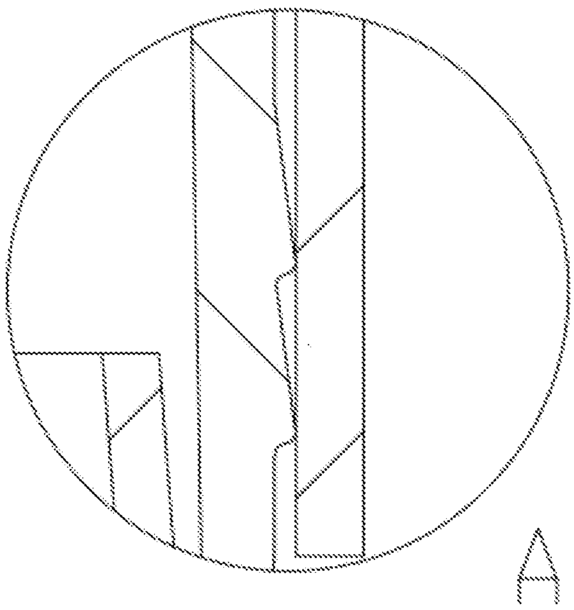
FIG. 9 is a schematic view illustrating a fixing position between a elastic membrane bladder and a medicament guiding tube at area A of FIG. 7.

Based on the elastic medicament liquid chamber 3 mentioned above, as a preferred solution, the elastic medicament liquid chamber 3 comprises the combination and fixation of the elastic membrane bladder 32 and the medicament guiding tube 31, as shown in FIG. 7 and FIG. 9.

The outer wall of the medicament guiding tube 31 is provided with one or more protruding rings for fixing and sealing the elastic membrane bladder 32.

Correspondingly, The end walls of the elastic membrane bladder 32 are thicker, and in the normal state, the inner diameter of the elastic membrane bladder 32 is smaller than the outer diameter of the wrapped portion of the medicament guiding tube 31, and the elastic membrane bladder 32 is tightly wound around the protruding rings at the outer side of the outer wall of the medicament guiding tube 31; the middle wall of the elastic membrane bladder 32 is thinner and is covering and wrapping the outer side of the liquid passage hole 311 in the middle section of the medicament guiding tube 31.

In this preferred embodiment, the protruding ring can be embodied to have a pagoda interface, and the orientation of the pagoda interface is toward the liquid passage hole 311, so as to obtain higher resistance. In order to balance the force on the elastic membrane bladder 32, the protruding rings are evenly and equidistantly distributed on both sides of the liquid passage hole 311.

Referring to FIGS. 10 and 11, when the medicament enters the medicament delivering vessel 3 from the medicament feeding unit 2 and flows into the elastic membrane bladder 32 through the liquid passage hole 311, the elastic membrane bladder 32 is inflated and forces are applied towards the center with contraction at both ends. The protruding rings on both sides of the liquid passage hole 311 will hinder the movement trend of the elastic membrane bladder 32. Under normal conditions, the inner diameter of the elastic membrane bladder 32 is smaller than the outer diameter of the wrapped portion of the medicament guiding tube 31, so when the elastic membrane bladder 32 is set on the medicament guiding tube 31, the ends of the elastic membrane bladder 32 will be in an expanded state. In addition, due to the thickness of the elastic membrane bladder 32 itself, it can have increased frictional force to fix the positions of both ends.

The elastic membrane bladder 32 has a thin middle wall and good expandability, which facilitates the storage of medicament when it is injected and reduces the resistance received by the syringe. It also provides hydraulic pressure for the dynamic medicament liquid, which is more conducive to the operation of the atomizing unit 4. In order for meeting the above conditions, the elastic membrane bladder 32 can be made of PET or silicone material.

Based on the above, in this embodiment of the present invention, the atomizing unit 4 is preferably embodied as a vibrating mesh with mesh holes, and the positive and negative electrodes of the vibrating mesh are electrically connected to a socket interface on a side wall of the housing 1.

In order to provide a suitable working space for the atomizing unit 4, an elastic sealing ring is installed on the contact surface between the atomizing unit 4 and the outer shell 1, another elastic sealing ring is installed on the contact surface between the atomizing unit 4 and the medicament guiding tube 31. The working mode of the vibrating mesh of the atomizing unit 4 is vibration, and the elastic sealing ring can still have a sealing effect while ensuring the vibration environment of the vibrating mesh, especially on the contact surface with the medicament guiding tube 31. Once the elastic sealing ring fails to seal, it will cause internal medicament contamination and medicament leakage.

Due to the fact that in this device, the medicament feeding unit 2 and the medicament delivering vessel 3 inside the outer shell 1 are fixed by the outer shell 1, there is a certain gap between them. In order to prevent the liquid from flowing out, a sealing ring is provided on the connecting surface between the medicament feeding unit 2 and the medicament delivering vessel 3.

Referring to FIG. 1, the outer shell 1 serves to fix the internal structure and is connected with the breathing circuit arrangement. In order to facilitate the connection with the breathing circuit arrangement, the outer shell 1 is provided with an air inlet connection port and an air outlet connection port, which are connected in series in the breathing circuit arrangement. In this solution, the connection position can be located at one end close to the patient. When connecting, there is no need for other external devices. Two pipelines can be respectively connected to the pipe opening formed at the top of the outer shell 1, so as to complete the connection.

Referring to FIGS. 15 to 34 of the drawings, an universal atomizer 100 according to a second preferred embodiment of the present invention is illustrated, the universal atomizer 100 comprises an outer shell 110, a medicament feeding unit 120, a medicament delivering vessel 130 communicated to the medicament feeding unit 120, an atomizing unit 140, and a depressurization receptacle 150 communicated to the medicament delivering vessel 130. The medicament liquid is fed into the medicament delivering vessel 130 through the medicament feeding unit 120 and guided to the atomizing unit 140 through the depressurization receptacle 150 which is communicated to the medicament delivering vessel 130, so that the medicament liquid is atomizing by the atomizing unit 140 to produce a medicament mist that can be fed to a breathing circuit arrangement 200.

According to the present invention, the medicament delivering vessel 130 is able to generate an elastic driving force for causing the medicament liquid in the medicament delivering vessel 130 to be delivered towards the atomizing unit 140.

More specifically, the medicament delivering vessel 130 comprises a medicament guiding tube 131 which is communicated to the medicament feeding unit 120 and an elastic membrane bladder 132 which is wound and wrapped around the medicament guiding tube 131 in a manner that the medicament liquid fed into the medicament guiding tube 131 is able to reach an inflating chamber 1320 between the clastic membrane bladder 132 and the medicament guiding tube 131, so as to inflate the elastic membrane bladder 132, so that the elastic membrane bladder 132 is inflated and deformed to generate the elastic driving force for causing the medicament liquid to be continually forced into the depressurization receptacle 150 and finally reach to the atomizing unit 140.

As shown in FIGS. 19-20, 22-23, 28-29, the medicament guiding tube 131 has a guiding channel 1311 and one or more, such as two liquid passage holes 1311 formed at two opposite sides of a middle section thereof and communicated to the guiding channel 1310, so that the medicament liquid in the medicament guiding tube 131 is able to enter the inflating chamber 1320 between the clastic membrane bladder 132 and the medicament guiding tube 131 through the liquid passage holes 1311, so as to increase the pressure in the inflating chamber 1320 and accumulate the elastic potential energy of the clastic membrane bladder 132. When the medicament liquid reaching to the atomizing unit 140 is atomized to produce the medicament mist, the elastic restoring force of the medicament guiding tube 131 is continually applied to the medicament liquid stored in the inflating chamber 1320, so as to continually drive the medicament liquid stored in the inflating chamber 1320 to flow back into the medicament guiding tube 131 through the liquid passage holes 1311 which penetrate through a thickness of the medicament guiding tube 131, so as to be further guided to the atomizing unit 140 through the depressurization receptacle 150 for the atomizing process.

In other words, when the medicament liquid is fed into the medicament guiding tube 131, the medicament liquid will not directly pass through the atomizing unit 140 to be discharged. Instead, the medicament liquid will be temporarily stored in the inflating chamber 1320 of the elastic membrane bladder 132 to cause the elastic membrane bladder 132 to deform and inflate to accumulate the elastic potential energy. When the atomizing unit 140 is in operation to generate the medicament mist by the medicament liquid reaching to the atomizing unit 140, the medicament liquid stored in the inflating chamber 1320 between the elastic membrane bladder 132 and the medicament guiding tube 131 will be gradually fed towards the atomizing unit 140. The elastic membrane bladder 132 will gradually deflate because of the reducing volume of the medicament liquid in the inflating chamber 1320 and the elastic restoring force of the elastic membrane bladder 132 due to its own elasticity will drive the medicament liquid in the inflating chamber 1320 to be continually fed towards the atomizing unit 140.

The elastic membrane bladder 132 can be made of but not limited to silicon material or or polyethylene terephthalate. A thickness of the elastic membrane bladder 132 is preferably 0.08-0.8 mm, and the actual amount of medicament liquid that can be accommodated in the inflating chamber 1320 is 5 ml-20 ml. The internal hydraulic pressure is 0-170 mmHg. The commonly used amount of medicament liquid for patients is 10 ml, and the hydraulic pressure inside the elastic membrane bladder 132 is 115-140 mmHg.

Figure 24:
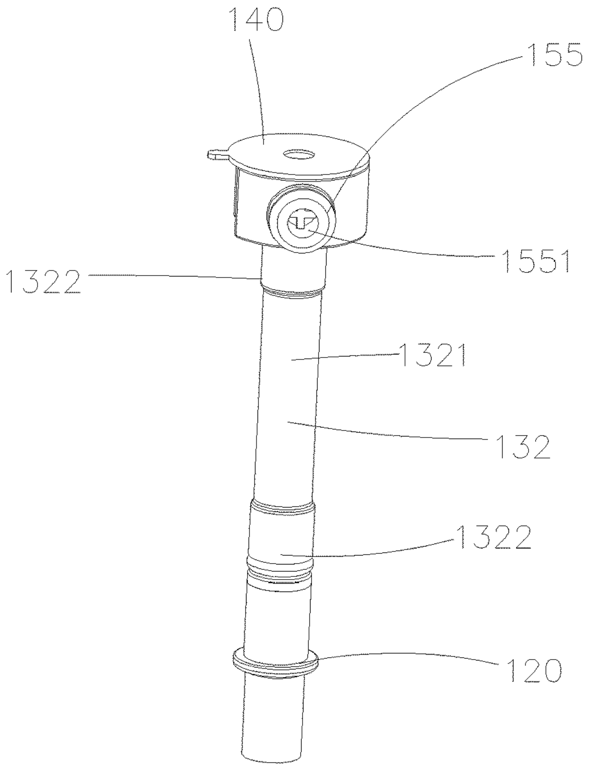
FIG. 24 is a perspective view illustrating an elastic membrane bladder of the universal atomizer being in a shrinking state according to the second preferred embodiment of the present invention.
Figure 25:
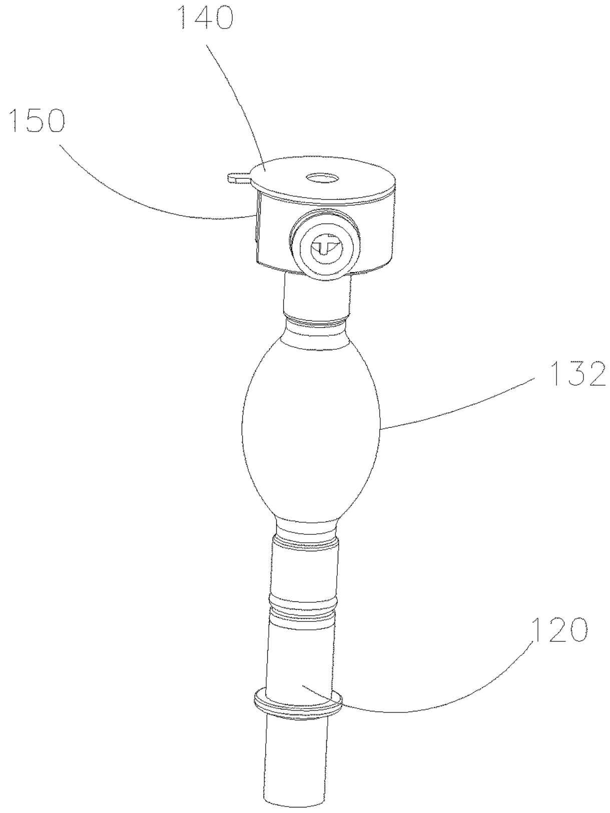
FIG. 25 is a perspective view illustrating an elastic membrane bladder of the universal atomizer being in an inflated state according to the second preferred embodiment of the present invention.
Figure 26:
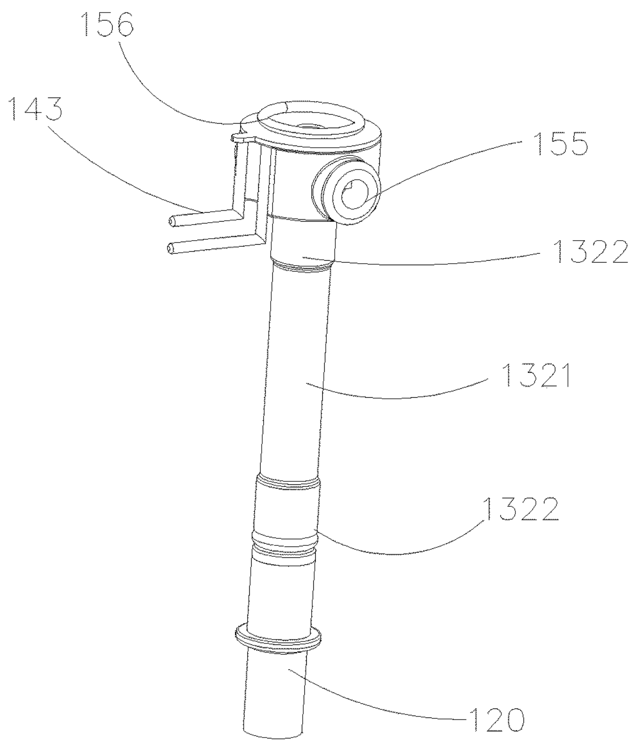
FIG. 26 is a perspective view illustrating an atomizing assembly of the universal atomizer according to the second preferred embodiment of the present invention.
Figure 27:
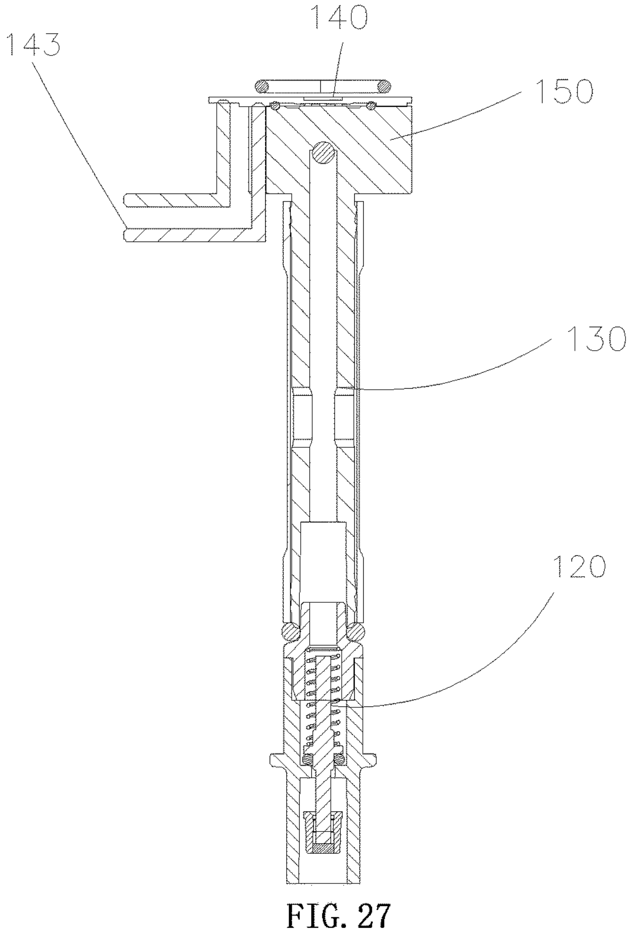
FIG. 27 is a sectional view illustrating the atomizing assembly of the universal atomizer according to the second preferred embodiment of the present invention.

As shown in FIGS. 24 and 26, the elastic membrane bladder 132 comprises a middle section 1321 and two end sections 1322 which are respectively provided at the two ends of the middle section 132. The middle section 1321 has a smaller thickness than the thickness of the two end sections 1322, so that the middle section 1321 is easy to deform when the medicament liquid is injected and inflated into the inflating chamber 1320. The two thicker end sections 1322 are firmly wrapped around the two end portions of the medicament guiding tube 131 to enhance the frictional contact between the elastic membrane bladder 132 and the medicament guiding tube 131, so as to stably retain the elastic membrane bladder 132 on the medicament guiding tube 131.

Preferably, the middle section 1321 of the elastic membrane bladder 132 may have an inner diameter than is slightly less than an outer diameter of the medicament guiding tube 131, so as to further enhance the firmly engagement between the medicament guiding tube 131 and the elastic membrane bladder 132.

The medicament guiding tube 131 may further comprise a plurality of retaining rings 1312 which are provided at each of the two end portions thereof for retaining the elastic membrane bladder 132. Accordingly, the retaining rings 1312 are spacedly arranged so as to enhance the frictional contact with the end portions 1322 of the elastic membrane bladder 132.

In addition, preferably, each of the retaining rings has a diameter that is gradually reducing towards the liquid passage hole 1311, so as to hook the end portions 1322 of the elastic membrane bladder 132 in position.

Since the atomizing unit 140 of this embodiment needs to work by means of electronic ultrasonic oscillation, the depressurization receptacle 150 is employed to provide a pressure relief effect, so as to avoid an excessive pressure of the medicament liquid around the atomizing unit 140 which will cause the atomizing unit 140 to not effectively function.

As shown in FIGS. 19-21 and 26-29, the depressurization receptacle 150 is connected to the medicament guiding tube 131. Accordingly, the depressurization receptacle 150 can be integrally extended from the medicament guiding tube 131 or is assembled with the medicament guiding tube 131. In this embodiment, the depressurization receptacle 150 is integrally extended from the medicament guiding tube 131 to actually from an end portion of the medicament guiding tube 131.

The depressurization receptacle 150 has a curved medicament delivery passage 151 for dividing liquid flows or forming dead water zones or vortex zones due to changes in cross-section or the presence of corners, so as to achieve the pressure loss of the medicament liquid in the depressurization receptacle 150.

More specifically, the depressurization receptacle 150 comprises a receptacle body 152 which is integrally extended from the medicament guiding tube 131 and the receptacle body 152 is a hollow structure that forms a receiving chamber 1511 which is communicated to the guiding channel 1310 of the medicament guiding tube 131, one or more side channels 1512 communicated to the receiving chamber 1511, one or more branch channels 1513 communicated to the receiving chamber 1511 for delivering the medicament liquid to the atomizing unit 140.

The receptacle body 152 has an end surface 1521 facing towards the atomizing unit 140, the depressurization receptacle 150 further comprises a plurality of diversion protrusions 153 integrally protruded from the end surface 1521 for defining an atomizing area 1514 which is a space within the plurality of diversion protrusions 153 and a plurality of diversion channels 1515 formed between two adjacent diversion protrusions 153.

Accordingly, the curved medicament delivery passage 151 of this embodiment comprises the receiving chamber 1511 which is communicated to the guiding channel 1310 of the medicament guiding tube 131, the side channels 1512 communicated to the receiving chamber 1511, the branch channels 1513 communicated to the receiving chamber 1511 for delivering the medicament liquid to the atomizing area 1514, the atomizing area 1514, and the diversion channels

1515 between two adjacent diversion protrusions 153. The medicament liquid in the guiding channel 1310 of the medicament guiding tube 131 will enter the receiving chamber 1511, and then is guided into the branch channels 1513, and reach the atomizing area 1514 by passing through the diversion channels 1515. The atomizing unit 140 is facing the atomizing area 1514, so that the medicament liquid in the atomizing area 1514 will be atomized to produce the atomized medicament mist.

In this embodiment, as an example, the receptacle body 152 has two side channels 1512 which are transversely extended from the receiving chamber 1511, two branch channels 113 communicated to the receiving chamber 1511, six diversion protrusions 153 protruded from the end surface 1521 to define six diversion channels 1515 distributed along a circumferential direction and a central atomizing area 1514 communicated to the six diversion channels 1515, so that dead water zones or vortex zones are formed to result in pressure loss.

Figure 28:
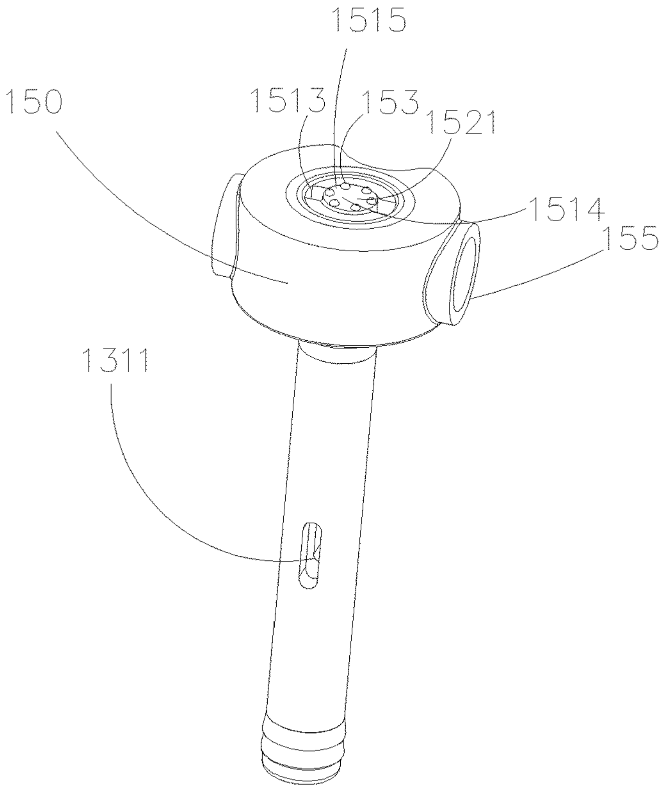
FIG. 28 is a perspective view illustrating a depressurization receptacle of the universal atomizer according to the second preferred embodiment of the present invention.

As shown in FIG. 28, the six diversion channels 1515 are grouped in pairs, and the liquid flows collide and cancel each other out, so as to form a balance zone in the central atomizing area 1514. In this balance zone, from the outside to the center, the pressure gradually decreases, and the liquid flow also slows down gradually. The atomizing area 1514 defines a working area of the atomizing unit 140, so that the medicament liquid at the center is efficiently atomized.

Figure 30:
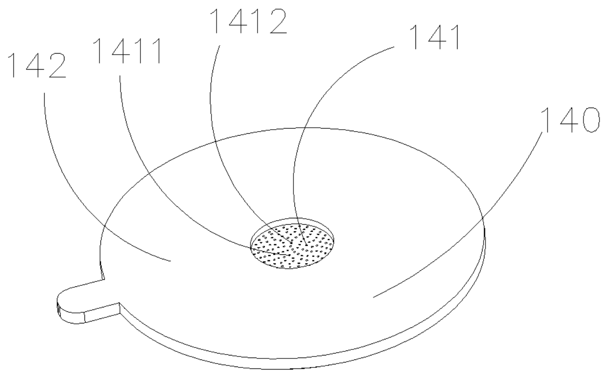
FIG. 30 is a perspective view illustrating an atomizing unit of the universal atomizer according to the second preferred embodiment of the present invention.
Figure 31:
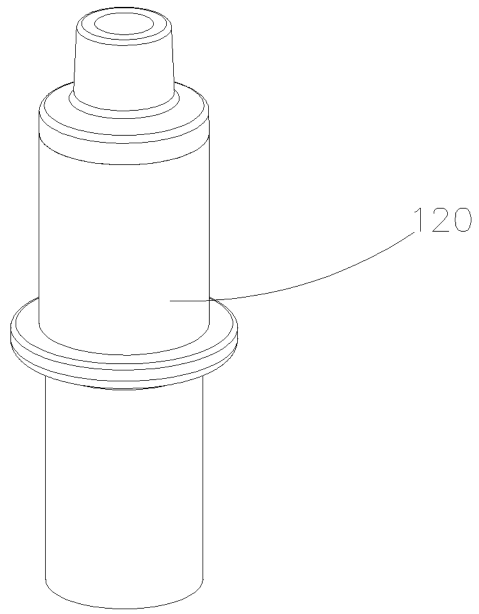
FIG. 31 is a perspective view of a medicament feeding unit of the universal atomizer according to the second preferred embodiment of the present invention.
Figure 32:
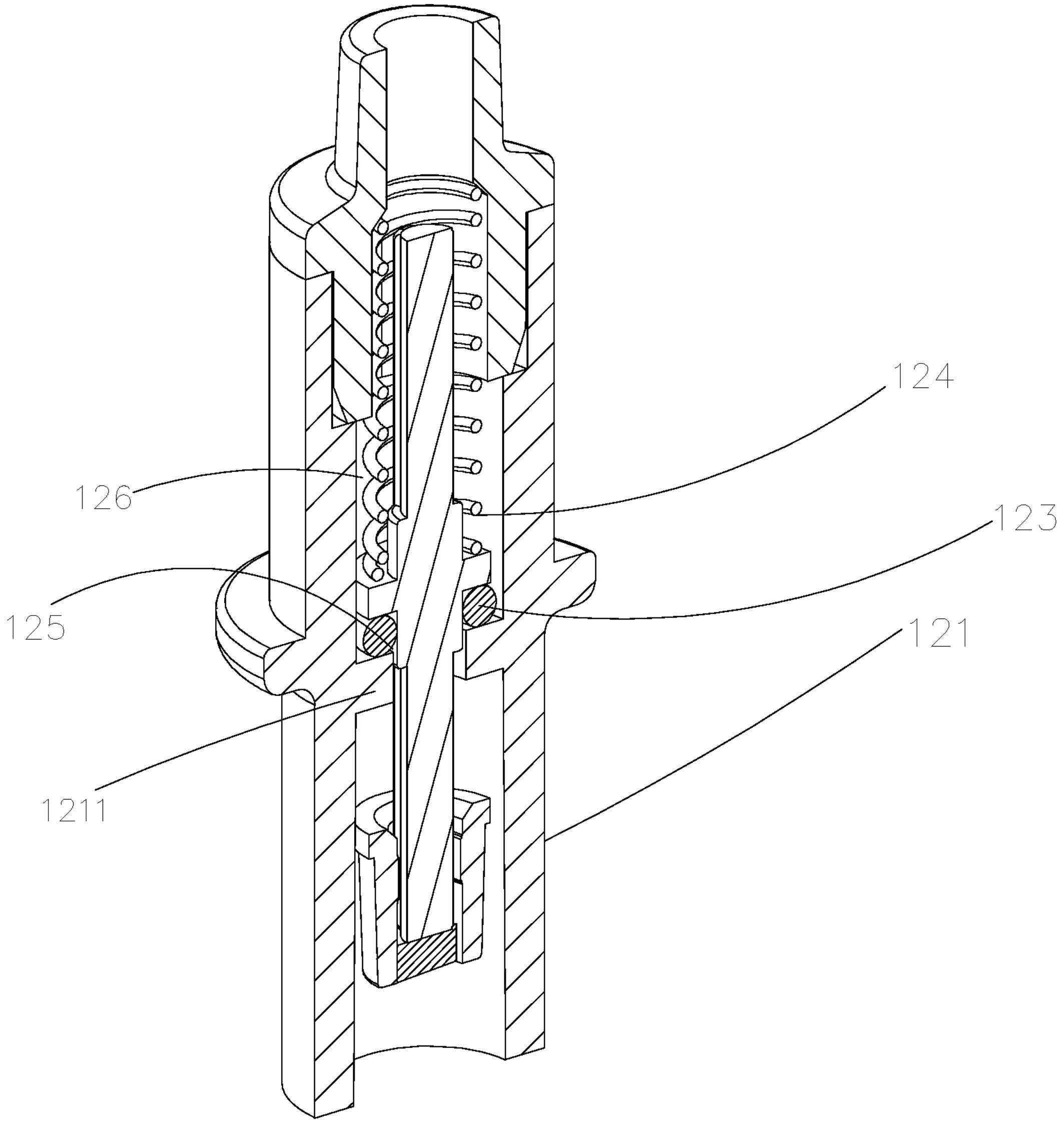
FIG. 32 is a schematic view illustrating the medicament feeding unit of the universal atomizer according to the second preferred embodiment of the present invention.
Figure 33:
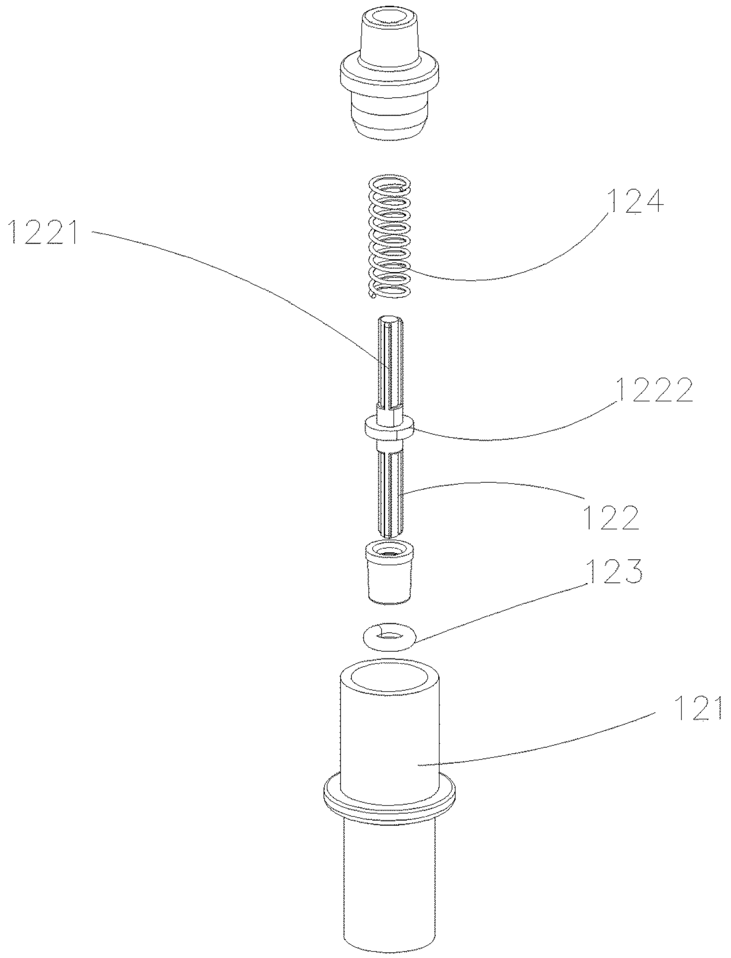
FIG. 33 is an exploded view of the medicament feeding unit of the universal atomizer according to the second preferred embodiment of the present invention.
Figure 34:
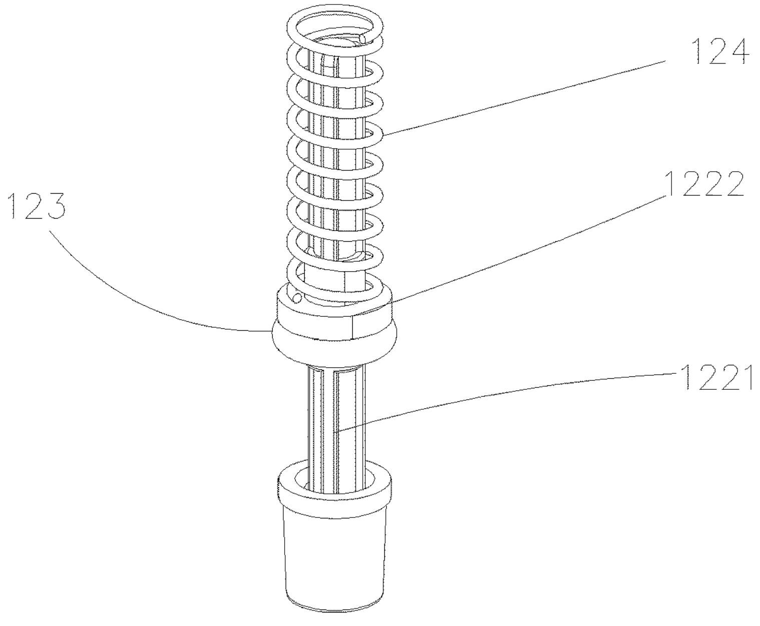
FIG. 34 is a perspective view illustrating a sealing plunger and a resilient valve ring of the medicament feeding unit of the universal atomizer according to the second preferred embodiment of the present invention.

Referring to FIG. 30, the atomizing unit 140 can be embodied as a vibrating mesh comprising an atomizing layer 141, a ring-shaped piezoelectric ceramic layer 142, and two electrode terminals 143 electrically connected to the atomizing layer 141 and the piezoelectric ceramic layer 142 respectively. In this embodiment, the atomizing layer 141 is an electrical conducting layer, the atomizing layer 141 and the piezoelectric ceramic layer 142 are respectively electrically connected to two opposite electrodes of a driving circuit. The atomizing layer 141 has a central atomizing area 1411 having a plurality of pores 1412 aligned with the atomizing area 1514. When a driving voltage is input into the atomizing layer 141 and the piezoelectric ceramic layer 142 through the two electrode terminals 143, the atomizing layer 141 will be driven to vibrate, so as to produce the medicament mist which is discharged through the pores 1412.

Alternatively, an electrical insulation layer may be provided between the atomizing layer 141 and the piezoelectric ceramic layer 142, both of the two electrode terminals 143 are electrically connected to the piezoelectric ceramic layer 142, so that when the driving voltage is input into the piezoelectric ceramic layer 142, the vibration of the piezoelectric ceramic layer 142 will drive the atomizing layer 141 to vibrate.

The maximum pressure during normal operation of the atomizing unit 140 must be less than 155 mmHg. Once exceeded, it will cause difficulty in vibrating the atomizing layer 141. After the pressure loss through the medicament delivery channels 151, the pressure is generally maintained between 135-145 mmHg, so as to ensure the stable operation of the atomizing unit 140.

Figure 21:
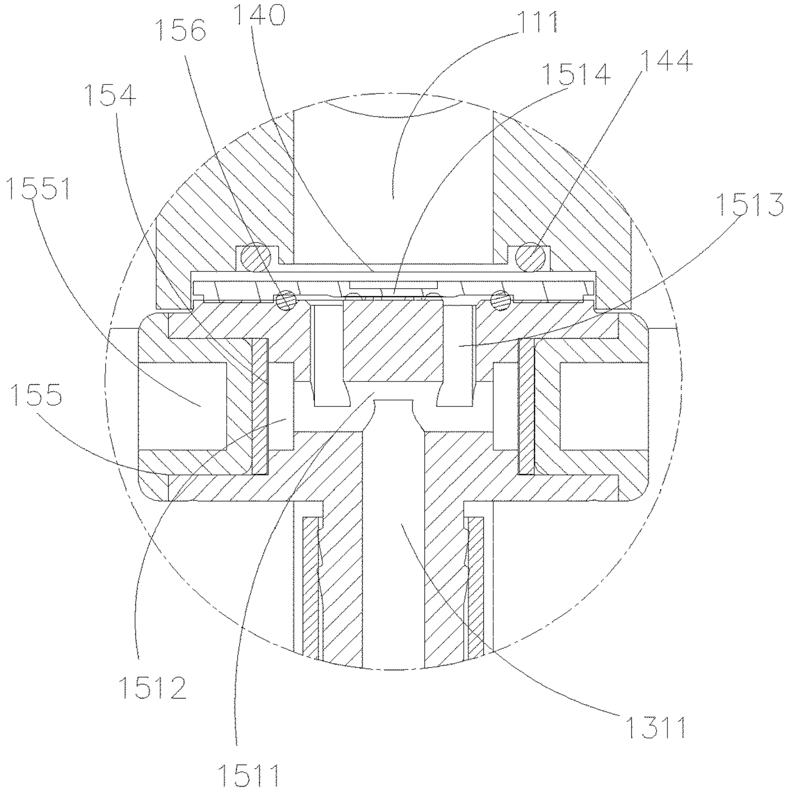
FIG. 21 is partial enlarged sectional view illustrating a curved medicament delivery passage of the universal atomizer according to the second preferred embodiment of the present invention.
Figure 22:
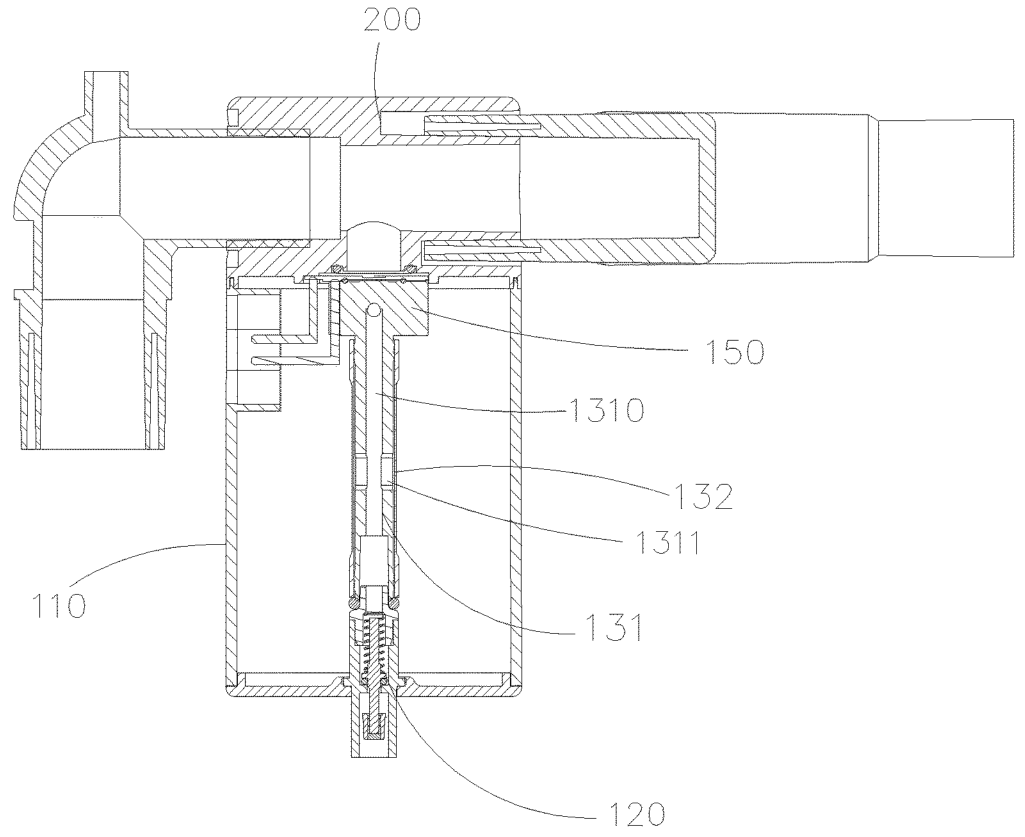
FIG. 22 is a sectional view of the universal atomizer being connected to a breathing circuit arrangement according to a second preferred embodiment of the present invention.
Figure 23:
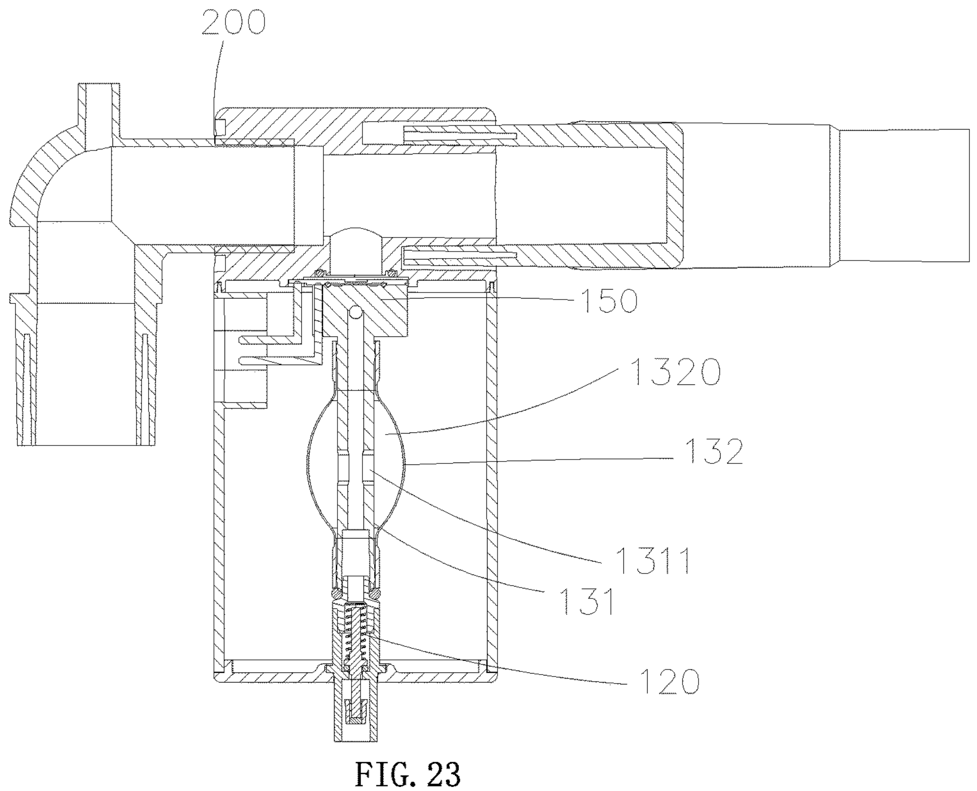
FIG. 23 is another sectional view of the universal atomizer being connected to the breathing circuit arrangement according to the second preferred embodiment of the present invention.
Figure 29:
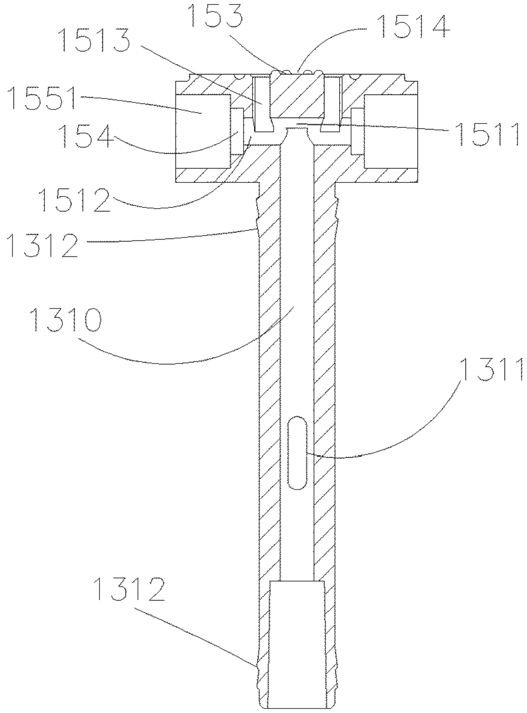
FIG. 29 is a sectional view illustrating the depressurization receptacle of the universal atomizer according to the second preferred embodiment of the present invention.

As shown in FIG. 21 and FIGS. 28-29, the depressurization receptacle 150 further comprises a gas permeable film 154 which is provided at each of the two side channels 1512, each of the two films 154 is a gas permeable but is water stopping, so as to allow air bubbles to pass through but prevent the medicament liquid to pass through. Correspondingly, the depressurization receptacle 150 further comprises two mounting members 155 each having a through hole 1551 communicating the receiving chamber 1511 to the outside. Each of the two mounting members 155 is arranged to mount the gas permeable film 154 at the corresponding side channel 1512.

Under normal circumstances, when atomization is occurring, the air entering the atomizing area 1514 will accumulate and affect the operation of atomizing unit 140. However, by setting diversion protrusions 153, the vibration of the atomizing layer 141 of the atomizing unit 104 will disperse the tiny bubbles and force the bubbles to flow into the branch channels 1513 through the diversion channels 1515, so as to reach the receiving chamber 1511, and finally be discharged through the gas permeable films 154 inside the side channels 1512, so that the amount of air remaining in the depressurization receptacle 150 is very small and will not affect the normal operation of the atomizing unit 140.

As shown in FIG. 21, the depressurization receptacle 150 further comprises a first sealing ring 156 which is a resilient ring that is provided between the atomizing unit 140 and the end surface 1521 of the receptacle body 152, so that the atomizing area 1514 and the diversion channels 1515 are sealed between the end surface 1521 of the receptacle body 142, the first sealing ring 154 and the atomizing layer 141 of the atomizing unit 140.

The atomizing unit 140 further comprises a second sealing ring 144 which is provided between the piezoelectric ceramic layer 142 and the inner wall of the outer shell 110, so as to prevent the leakage of the medicament mist.

The medicament feeding unit 120 is a medical valve structure comprising but not limited to a pressure injection valve, a three-way valve, a check valve, and an infusion switch. In this embodiment, the medicament feeding unit 120 adopts a pressure injection valve which is essentially a check valve structure.

More specifically, as shown in FIGS. 31-34, the medicament feeding unit 120 comprises a sealing housing 121 mounted to the outer shell 110, a sealing plunger 122 arranged in the sealing housing 121, a resilient valve ring 123, and a spring 124 which is connected to the sealing plunger 122 and the sealing housing 121. The sealing plunger 122 comprises a plunger rod 1221 and an abutting ring 1222 connected to the plunger rod 1221, the sealing housing 121 has an inner step 1211, the resilient valve ring 123 is a sealing ring provided between the inner step 1211 of the sealing housing 121 and the abutting ring 1222 of the sealing plunger 122, so that an injection port 125 of a feeding passage 126 between the sealing plunger 122 and the sealing housing 121 can be sealed by the resilient valve ring 123.

The structure of the pressure injection valve comprises a sealing housing embedded at an injection port of the outer shell for fixed connection with the outer shell 1, a sealing plunger arranged inside the sealing housing, and the sealing plunger is limited by a spring on one side inside the sealing housing.

During operation, when an syringe is inserted to supply the medicament liquid to the injection port 125 and drive the abutting ring 1222 of the sealing plunger 122 to bias against the spring 124, so as to compress the spring 124, and the resilient valve ring 123 is separated from the injection port 125, allowing the medicament liquid to flow into the feeding passage 126, so that the medicament liquid is fed into the medicament delivering vessel 120. When the syringe is removed from the injection port 125, the spring 124 returns to its original position, so as to restore the initial position of the resilient valve ring 123.

Figure 17:
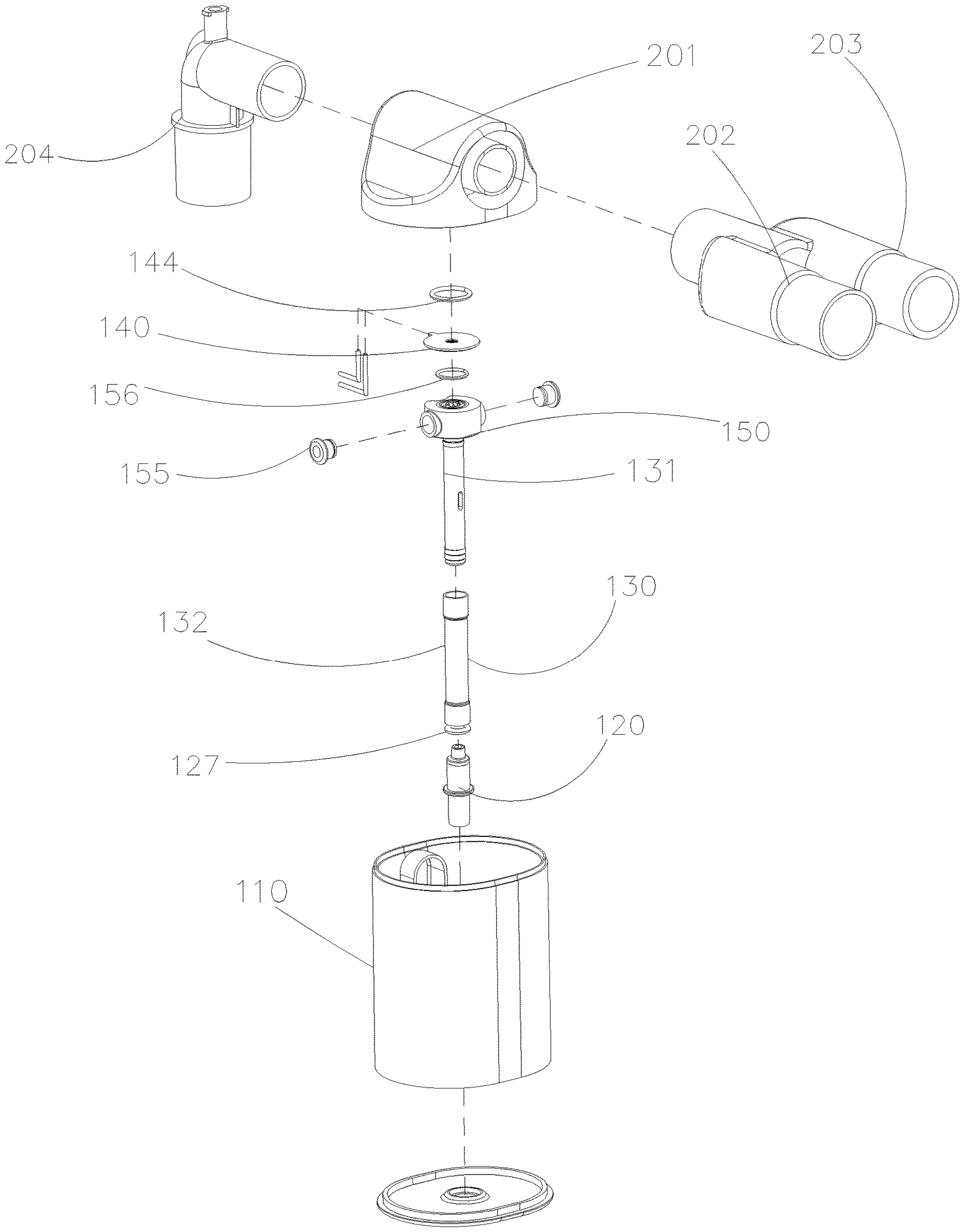
FIG. 17 is an exploded view of the universal atomizer being connected to the breathing circuit arrangement according to the second preferred embodiment of the present invention.
Figure 18:
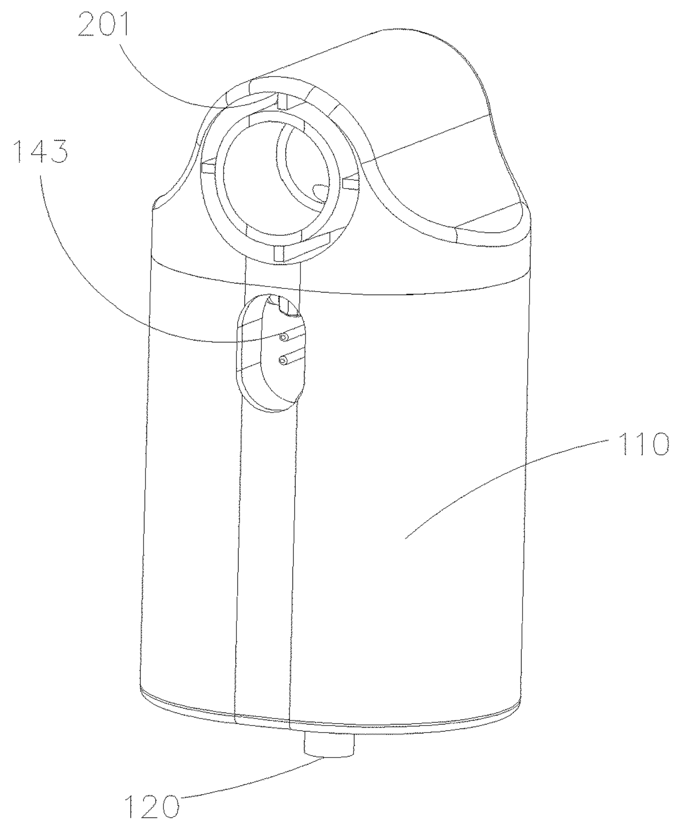
FIG. 18 is a perspective view of the universal atomizer according to the second preferred embodiment of the present invention.
Figure 19:
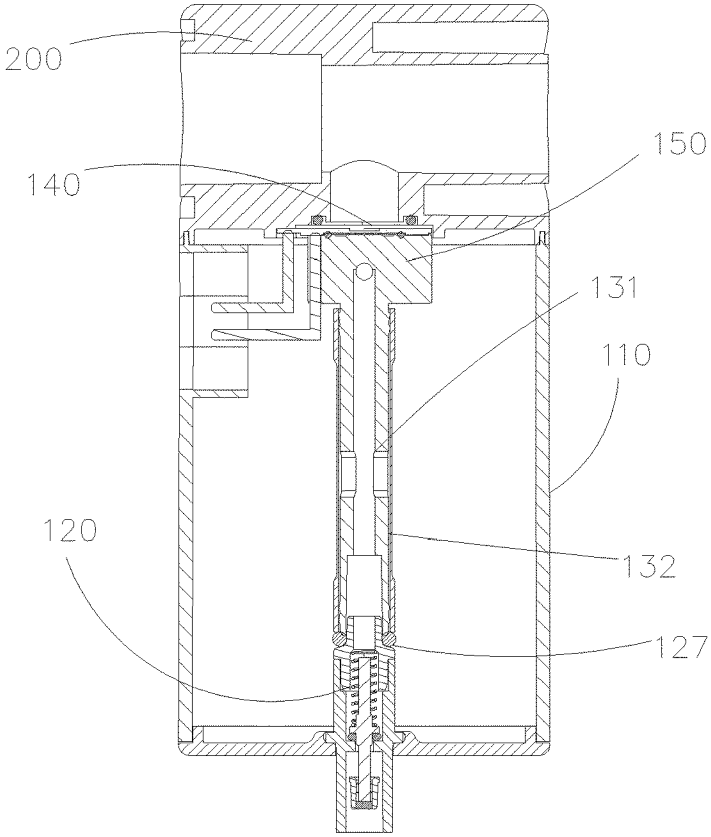
FIG. 19 is a sectional view of the universal atomizer according to the second preferred embodiment of the present invention.
Figure 20:
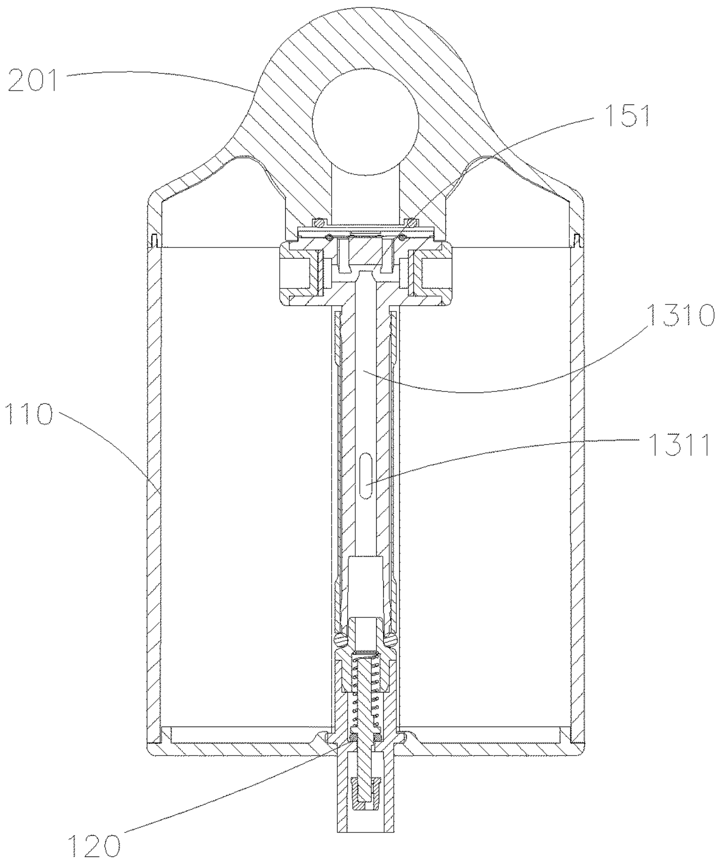
FIG. 20 is another sectional view of the universal atomizer according to the second preferred embodiment of the present invention.

As shown in FIG. 17 and FIG. 19, the medicament feeding unit 120 further comprises a third sealing ring 127 which is a resilient ring provided between the sealing housing 121 and the medicament guiding tube 131, so as to enhance the sealing effect between the sealing housing 121 and the medicament guiding tube 131.

The breathing circuit arrangement 200 comprises a connector 201, a gas feeding tube 202, a gas recycling tube 203, and a mist feeding tube 204 which can be connected to a trachea cannula or a breathing mask for feeding the medicament mist to the user. The connector 201 is connected to the outer shell 110 which has a mist outlet 111 for feeding the medicament mist into the inner cavity of the connector 201, the gas feeding tube 202 and the gas recycling tube 203 are connected to the connector 201 for feeding gas or recycling gas, and the mist feeding tube 204 is connected to the connector 201 for supplying the medicament mist to the user.

Accordingly, in this embodiment, when a volume of medicament liquid is injected into the medicament feeding unit 120, the medicament liquid will be guided into the guiding channel 1310 of the medicament guiding tube 131 through the feeding passage 126, and then enter the inflating chamber 1320 between the medicament guiding tube 131 and the elastic membrane bladder 132 through the liquid passage hole 1311, so as to inflate the elastic membrane bladder 132, and thus the medicament liquid can be stored in the elastic membrane bladder 132.

When the atomizing unit 140 is turned on for operation, the medicament liquid flow will flow back into the medicament guiding tube 131 through the liquid passage hole 1311 and is guided into the receiving chamber 1511 of the depressurization receptacle 150. And then the medicament liquid will flow into the atomizing area 1514 by passing through the branch channels 1513 and the diversion channels 1515, so that the medicament liquid is converged in the atomizing area 1514, and the flowing path of the medicament liquid will result in the pressure loss of the flow of the medicament liquid in the depressurization receptacle 150, so as to ensure a suitable pressure environment for the atomizing unit 140 which will atomize the medicament liquid in the atomizing area 1514 to produce the medicament mist which is feed into the breathing circuit arrangement 200 through the mist outlet 111.

The above embodiments are merely illustrative examples to explain the principles and effects of the present patent application, and are not intended to limit the scope of the present patent application. Anyone skilled in the art can modify or change the above embodiments without departing from the spirit and scope of the present patent application. Therefore, all equivalent modifications or changes made by those skilled in the art in the relevant technical field, based on the spirit and technical ideas disclosed in the present patent application, should still be covered by the claims of the present patent application.

What is claimed is:

1. An atomizer, comprising:

a medicament feeding unit;

a medicament delivering vessel; and an atomizing unit, wherein when medicament liquid is fed into the medicament delivering vessel through the medicament feeding unit, the medicament delivering vessel is capable of generating an elastic driving force for driving the medicament liquid to be fed towards the atomizing unit for atomizing the medicament liquid, the medicament delivering vessel comprises a medicament guiding tube communicated between the medicament feeding unit at one end of the medicament guiding tube and the atomizing unit at an opposite end of the medicament guiding tube, and an elastic membrane bladder wrapped around the medicament guiding tube, wherein an inflating chamber is defined between the elastic membrane bladder and the medicament guiding tube, wherein the medicament guiding tube has a guiding channel and one or more liquid passage holes communicating the guiding channel to the inflating chamber.

2. The atomizer, as recited in claim 1, wherein the elastic membrane bladder comprises a middle section and two end sections connected to two ends of the middle section, wherein a thickness of the middle section is smaller than a thickness of each of the two end sections.

3. The atomizer, as recited in claim 2, wherein the medicament guiding tube comprises one or more retaining rings at each of two ends thereof for frictional engagement with the corresponding end section of the elastic membrane bladder.

4. The atomizer, as recited in claim 3, wherein each of the one or more retaining rings has gradually reducing diameters along a direction towards the one or more liquid passage holes.

5. The atomizer, as recited in claim 1, wherein an inner diameter of the elastic membrane bladder is smaller than or equal to an outer diameter of the medicament guiding tube.

6. The atomizer, as recited in claim 1, wherein a material of the elastic membrane bladder is one of silicone material and polyethylene terephthalate.

7. The atomizer, as recited in claim 1, further comprising a depressurization receptacle connected to the medicament guiding tube, wherein the depressurization receptacle has a curved medicament delivery passage for causing pressure loss of the medicament liquid, wherein the curved medicament delivery passage is communicated to the medicament delivering vessel for feeding the medicament liquid toward the atomizing unit.

8. The atomizer, as recited in claim 7, wherein the curved medicament delivery passage comprises a receiving chamber communicated to the medicament delivering vessel and a plurality of branch channels communicated to the receiving chamber, and an atomizing area communicated to the plurality of branch channels, wherein the atomizing unit abuts the atomizing area.

9. The atomizer, as recited in claim 8, wherein an extending direction of each of the branch channels is vertical to a plane of the atomizing area.

10. The atomizer, as recited in claim 1, wherein the medicament feeding unit comprises a sealing housing, a sealing plunger arranged in the sealing housing, a resilient valve ring, and a spring which is connected to the sealing plunger and the sealing housing, wherein the medicament feeding unit has an injection port and a feeding passage, wherein the sealing plunger comprises a plunger rod and an abutting ring connected to the plunger rod, the sealing housing has an inner step, the resilient valve ring is provided between the inner step of the sealing housing and the abutting ring of the sealing plunger, so that injection port communication to the feeding passage between the sealing plunger and the sealing housing is capable of being sealed by the resilient valve ring.

11. The atomizer, as recited in claim 1, wherein the atomizing unit comprises an atomizing layer and a ring-shaped piezoelectric ceramic layer stacked on the atomizing layer.

12. An atomizer, comprising:

a medicament feeding unit;

a medicament delivering vessel; and an atomizing unit, wherein when medicament liquid is fed into the medicament delivering vessel through the medicament feeding unit, the medicament delivering vessel is capable of generating an elastic driving force for driving the medicament liquid to be fed towards the atomizing unit for atomizing the medicament liquid, further comprising a depressurization receptacle connected to the medicament guiding tube, wherein the depressurization receptacle has a curved medicament delivery passage for causing pressure loss of the medicament liquid, wherein the curved medicament delivery passage is communicated to the medicament delivering vessel for feeding the medicament liquid toward the atomizing unit, wherein the depressurization receptacle comprises a receptacle body comprising an end surface, and a plurality of diversion protrusions protruded from the end surface to define the atomizing area.

13. The atomizer, as recited in claim 12, wherein the curved medicament delivery passage comprises a plurality of diversion channels each is formed between two adjacent diversion protrusions.

14. The atomizer, as recited in claim 13, wherein the plurality of diversion channels is configured in a manner that liquid flows of the medicament liquid collide with each other to form a balance zone in the atomizing area at a center of the plurality of diversion channels arranged in a circumferential direction.

15. The atomizer, as recited in claim 13, wherein the plurality of diversion channels is evenly distributed along the circumferential direction and allow the liquid flows to converge in a same plane of the atomizing area.

16. The atomizer, as recited in claim 13, wherein the plurality of diversion channels is grouped in pairs, where the two diversion channels of each pair are symmetrically arranged with each other.

17. The atomizer, as recited in claim 12, wherein the depressurization receptacle further comprises a first sealing ring provided between the end surface of the receptacle body and the atomizing unit, wherein the atomizing area is formed within the first sealing ring.

18. An atomizer, comprising:

a medicament feeding unit;

a medicament delivering vessel; and an atomizing unit, wherein when medicament liquid is fed into the medicament delivering vessel through the medicament feeding unit, the medicament delivering vessel is capable of generating an elastic driving force for driving the medicament liquid to be fed towards the atomizing unit for atomizing the medicament liquid, further comprising a depressurization receptacle connected to the medicament guiding tube, wherein the depressurization receptacle has a curved medicament delivery passage for causing pressure loss of the medicament liquid, wherein the curved medicament delivery passage is communicated to the medicament delivering vessel for feeding the medicament liquid toward the atomizing unit, wherein the curved medicament delivery passage further comprises one or more side channels communicated to the receiving chamber, wherein each of the one or more side channels is provided with a gas permeable film that is water stopping for dispersing air bubbles generated in the depressurization receptacle to an outside of the atomizer.

19. The atomizer, as recited in claim 18, wherein the depressurization receptacle further comprises one or more mounting members for mounting the one or more gas permeable films at the one or more side channels respectively, wherein each of the one or more mounting members has a through hole for communicating the corresponding gas permeable film to the outside.

* * * * *